(12) United States Patent
Mather et al.

(10) Patent No.: US 7,718,774 B2
(45) Date of Patent: May 18, 2010

(54) TES7 AND ANTIBODIES THAT BIND THERETO

(75) Inventors: Jennie P. Mather, Millbrae, CA (US); Tony W. Liang, San Mateo, CA (US)

(73) Assignee: MacroGenics, Inc., Rockville, MD (US)

( * ) Notice: Subject to any disclaimer, the term of this patent is extended or adjusted under 35 U.S.C. 154(b) by 0 days.

(21) Appl. No.: 11/937,470

(22) Filed: Nov. 8, 2007

(65) Prior Publication Data

US 2008/0226634 A1    Sep. 18, 2008

Related U.S. Application Data

(60) Provisional application No. 60/858,113, filed on Nov. 8, 2006, provisional application No. 60/993,882, filed on Sep. 14, 2007.

(51) Int. Cl.
*C07K 16/30* (2006.01)
*A61K 39/395* (2006.01)
*G01N 33/53* (2006.01)

(52) U.S. Cl. .................. 530/387.1; 424/130.1; 435/7.1

(58) Field of Classification Search ....................... None
See application file for complete search history.

(56) References Cited

U.S. PATENT DOCUMENTS

| | | | |
|---|---|---|---|
| 3,842,067 A | 10/1974 | Sarantakis | |
| 3,862,925 A | 1/1975 | Sarantakis et al. | |
| 3,972,859 A | 8/1976 | Fujino et al. | |
| 4,105,603 A | 8/1978 | Vale, Jr. et al. | |
| RE30,548 E | 3/1981 | Vale, Jr. et al. | |
| 4,816,567 A | 3/1989 | Cabilly et al. | |
| 5,565,332 A | 10/1996 | Hoogenboom et al. | |
| 5,580,717 A | 12/1996 | Dower et al. | |
| 5,656,444 A | 8/1997 | Webb et al. | |
| 5,733,743 A | 3/1998 | Johnson et al. | |
| 5,807,715 A | 9/1998 | Morrison et al. | |
| 5,866,692 A | 2/1999 | Shitara et al. | |
| 5,997,867 A | 12/1999 | Waldmann et al. | |
| 6,054,297 A | 4/2000 | Carter et al. | |
| 6,054,561 A | 4/2000 | Ring | |
| 6,180,377 B1 | 1/2001 | Morgan et al. | |
| 6,265,150 B1 | 7/2001 | Terstappen et al. | |
| 6,331,415 B1 | 12/2001 | Cabilly et al. | |
| 6,429,303 B1 | 8/2002 | Green et al. | |
| 6,891,030 B2 | 5/2005 | Chen | |
| 6,965,018 B2 | 11/2005 | Mikesell et al. | |
| 7,527,969 B2 * | 5/2009 | Mather et al. ............... 435/325 |
| 2002/0081305 A1 | 6/2002 | Mayumi et al. | |
| 2003/0039999 A1 | 2/2003 | Yoshinaga et al. | |
| 2003/0134283 A1 | 7/2003 | Peterson et al. | |
| 2003/0162186 A1 | 8/2003 | Bejanin et al. | |
| 2004/0037833 A1 | 2/2004 | Mather et al. | |
| 2004/0077043 A1 | 4/2004 | Watarai et al. | |
| 2004/0162236 A1 | 8/2004 | Alsobrook, II et al. | |
| 2004/0236088 A1 | 11/2004 | Heuer et al. | |
| 2005/0002935 A1 | 1/2005 | Ling et al. | |
| 2005/0070474 A1 | 3/2005 | Krissansen et al. | |
| 2005/0090440 A1 | 4/2005 | Krissansen et al. | |
| 2005/0202536 A1 | 9/2005 | Chen | |
| 2006/0154313 A1 | 7/2006 | Anderson et al. | |
| 2006/0275287 A1 | 12/2006 | St Croix et al. | |
| 2007/0122378 A1 | 5/2007 | Freeman et al. | |
| 2007/0172504 A1 | 7/2007 | Shirwan et al. | |
| 2007/0184473 A1 | 8/2007 | Shirwan et al. | |
| 2007/0202566 A1 | 8/2007 | Bornscheuer et al. | |
| 2007/0292885 A1 | 12/2007 | Bejanin et al. | |

FOREIGN PATENT DOCUMENTS

| | | |
|---|---|---|
| EP | 0 519 596 B1 | 2/2005 |
| WO | WO-00/68266 A1 | 11/2000 |
| WO | WO-01/14557 A1 | 3/2001 |
| WO | WO-01/14557 B1 | 3/2001 |
| WO | WO-01/43869 A2 | 6/2001 |
| WO | WO-01/43869 A3 | 6/2001 |
| WO | WO-01/89567 A1 | 11/2001 |
| WO | WO-02/099119 A2 | 12/2002 |
| WO | WO-02/099119 A3 | 12/2002 |
| WO | WO-2004/001004 A2 | 12/2003 |
| WO | WO-2004/001381 A2 | 12/2003 |
| WO | WO-2004/001381 A3 | 12/2003 |
| WO | WO-2004/001381 C1 | 12/2003 |
| WO | WO-2004/007527 A2 | 1/2004 |
| WO | WO-2004/007527 A3 | 1/2004 |
| WO | WO-2004/023973 A2 | 3/2004 |
| WO | WO-2004/023973 A3 | 3/2004 |
| WO | WO-2005/017163 A2 | 2/2005 |
| WO | WO-2005/017163 A3 | 2/2005 |
| WO | WO-2005/032496 A2 | 4/2005 |
| WO | WO-2006/016276 A2 | 2/2006 |
| WO | WO-2006/096834 A2 | 9/2006 |
| WO | WO-2006/096834 C1 | 9/2006 |
| WO | WO-2007/146968 A2 | 12/2007 |

OTHER PUBLICATIONS

Aruffo, A. et al. (Dec. 1987). "Molecular Cloning of a CD28 cDNA by a High-Efficiency COS Cell Expression System," *Proceedings of the National Academy of Sciences USA* 84:8573-8577.

Bird, R.E. et al. (Oct. 21, 1988). "Single-Chain Antigen-Binding Proteins," *Science* 242(4877):423-426.

Brown, B.A et al. (Jul. 1, 1987). "Tumor-Specific Genetically Engineered Murine/Human Chimeric Monoclonal Antibody," *Cancer Research* 47:3577-3583.

Carter, P. et al. (May 1992). "Humanization of an Anti-p185$^{HER2}$ Antibody for Human Cancer Therapy," *Proceedings of the National Academy of Sciences USA* 89:4285-4289.

(Continued)

*Primary Examiner*—Ilia Ouspenski
(74) *Attorney, Agent, or Firm*—Jeffrey I. Auerbach; Edell, Shapiro & Finnan, LLC

(57) ABSTRACT

The invention provides the identification and characterization of disease and cancer-associated antigen, TES7. The invention also provides a family of monoclonal antibodies that bind to antigen TES7, methods of diagnosing and treating various human cancers and diseases that express TES7.

22 Claims, 12 Drawing Sheets

OTHER PUBLICATIONS

Castriconi, R. et al. (Aug. 24, 2004). "Identification of 4Ig-B7-H3 as a Neuroblastoma-Associated Molecule that Exerts a Protective Role From an NK Cell-Mediated Lysis," *Proceedings of the National Academy of Sciences USA* 101(34):12640-12645.

Co, M.S. et al. (Apr. 1991). "Humanized Antibodies for Antiviral Therapy," *Proceedings of the National Academy of Sciences USA* 88:2869-2873.

Co, M.S. et al. (Feb. 15, 1992). "Chimeric and Humanized Antibodies with Specificity for the CD33 Antigen," *The Journal of Immunology* 148(4):1149-1154.

Daugherty, B.L. et al. (1991). "Polymerase Chain Reaction Facilitates the Cloning, CDR-Grafting, and Rapid Expression of a Murine Monoclonal Antibody Directed Against the CD18 Component of Leukocyte Integrins," *Nucleic Acids Research* 19(9):2471-2746.

Gorman, S.D. et al. (May 1991). "Reshaping a Therapeutic CD4 Antibody," *Proceedings of the National Academy of Sciences USA* 88:4181-4185.

Houghten, R.A. (Aug. 1985). "General Method for the Rapid Solid-Phase Synthesis of Large Numbers of Peptides: Specificity of Antigen-Antibody Interaction at the Level of Individual Amino Acids," *Proceedings of the National Academy of Sciences USA* 82:5131-5135.

Jones, P.T. et al. (May 29, 1986). "Replacing the Complementarity-Determining Regions in a Human Antibody With Those From a Mouse," *Nature* 321:522-525.

Kelley, R.F. et al. (1990). "Folding of Eukaryotic Proteins Produced in *Escherichia coli*," in *Genetic Engineering*, Setlow, J.K. ed., Plenum Press: New York, NY, 12:1-19.

Kettleborough, C.A. et al. (1991). "Humanization of a Mouse Monoclonal Antibody by CDR-Grafting: The Importance of Framework Residues on Loop Conformation," *Protein Engineering* 4(7):773-783.

Köhler, G. et al. (Aug. 7, 1975). "Continuous Cultures of Fused Cells Secreting Antibody of Predefined Specificity," *Nature* 256:495-497.

Lobuglio, A.F. et al. (Jun. 1989). "Mouse/Human Chimeric Monoclonal Antibody in Man: Kinetics and Immune Response," *Proceedings of the National Academy of Sciences USA* 86:4220-4224.

Lonberg, N. et al. (1995). "Human Antibodies from Transgenic Mice," *Int Rev. Immunol.* 13(2):65-93.

Maeda, H. et al. (Jul. 1991). "Construction of Reshaped Human Antibodies with HIV-Neutralizing Activity," *Human Antibodies and Hybridomas* 2:124-134.

Mangham, D.C. et al. (1999). "A Novel Immunohistochemical Detection System Using Mirror Image Complementary Antibodies (MICA)" *Histopathology* 35(2):129-133.

Merrifield, R.B. (Jul. 20, 1963). "Solid Phase Peptide Synthesis. I. The Synthesis of a Tetrapeptide," *Journal of the American Chemical Society* 85:2149-2154.

Peeters, K. et al. (2001). "Production of Antibodies and Antibody Fragments in Plants," *Vaccine* 19:2756-2761.

Pollock, D.P. et al. (1999). "Transgenic Milk as a Method for the Production of Recombinant Antibodies," *Journal of Immunological Methods* 231:147-157.

Riechmann, L. et al. (Mar. 24, 1988). "Reshaping Human Antibodies for Therapy," *Nature* 332:323-327.

Sato, K. et al. (Feb. 15, 1993). "Reshaping a Human Antibody to Inhibit the Interleukin 6-Dependent Tumor Cell Growth," *Cancer Research* 53:851-856.

Shaw, D.R. et al. (Jun. 15, 1987). "Characterization of a Mouse/Human Chimeric Monoclonal Antibody (17-1A) to a Colon Cancer Tumor-Associated Antigen," *The Journal of Immunology* 138:4534-4538.

Steinberger, P. et al. (Feb. 15, 2004). "Molecular Characterization of Human 4Ig-B7-HE, a Member of the B7 Family with Four Ig-Like Domains," *The Journal of Immunology* 172(4):2352-2359.

Stephan, J-P. et al. (1999). "Distribution and Function of the Adhesion Molecule BEN During Rat Development," *Developmental Biology* 212:264-277.

Stephan, J-P. et al. (1999). "Selective Cloning of Cell Surface Proteins Involved in Organ Development: Epithelial Glycoprotein is Involved in Normal Epithelial Differentiation," *Endocrinology* 140(12):5841-5854.

Sun, M. et al. (2002). "Characterization of Mouse and Human B7-H3 Genes," *The Journal of Immunology* 168:6294-6297.

Tempest, P.R. et al. (Mar. 1991). "Reshaping a Human Monoclonal Antibody to Inhibit Human Respiratory Syncytial Virus Infection In Vivo," *Bio/Technology* 9:266-271.

Verhoeyen, M. et al. (Mar. 25, 1988). "Reshaping Human Antibodies: Grafting an Antilysozyme Activity," *Science* 239:1534-1536.

Weiner, L.M. et al. (2001). "Therapeutic Monoclonal Antibodies: General Principles," Chapter 20 Section 5 in *Cancer: Principles and Practice of Oncology*, 6th Edition, Philadelphia, PA pp. 495-508.

Wheatley, S.P. et al. (1998). "Indirect Immunoflourescence Microscopy in Cultured Cells," Chapter 18 in *Methods in Cell Biology*, Mather, J.P. et al. eds., Academic Press: San Diego, CA, 57:313-332.

Winter, G. et al. (Jan. 24, 1991). "Man-Made Antibodies," *Nature* 349:293-299.

Winter, G. et al. (1994). "Making Antibodies by Phage Display Technology," *Annual Review of Immunology* 12:433-455.

Woodruff, T.K. (1998). "Cellular Localization of mRNA and Protein: In Situ Hybridization Histochemistry and in Situ Ligand Binding," Chapter 19 in *Methods in Cell Biology*, Mather, J.P. et al. eds., Academic Press: San Diego, CA, 57:333-351.

Banki, K. et al. (Jan. 28, 1994). "Cloning and Expression of the Human Gene for Transaldolase: A Novel Highly Repetitive Element Constitutes an Integral Part of the Coding Sequence," *The Journal of Biological Chemistry* 269(4):2847-2851.

Bendayan, M. et al. (1995). "Possibilities of False Immunocytochemical Results Generated by the Use of Monoclonal Antibodies: The Example of Anti-proinsulin Antibody," *The Journal of Histochemistry and Cytochemistry* 43(9):881-886.

Bodey, B. et al. (2000). "Failure of Cancer Vaccines: The Significant Limitations of this Approach to Immunotherapy," *Anticancer Research* 20:2665-2676.

Boon, T. (1992). "Toward a Genetic Analysis of Tumor Rejection Antigens," *Advances in Cancer Research* 58:177-210.

Chapoval, A.I. et al. (Mar. 2001). "B7-H3: A Costimulatory Molecule for T Cell Activation and IFN-γ Production," *Nature Immunology* 2(3):269-274.

Kirkin, A.F. et al. (1998). "Melanoma-Associated Antigens Recognized by Cytotoxic T Lymphocytes," *APMIS* 106:665-679.

Paul, W.E. ed. (1993). "Immunogenicity and Antigen Structure," In Chapter 8, In *Fundamental Immunology*, 3rd edition, Raven Press, Ltd.: New York, NY, pp. 242-243.

Smith, R.T. (Aug. 1994). "Cancer and the Immune System," *Clinical Immunology* 41 (4):841-849.

White, C.A. et al. (2001). "Antibody-Targeted Immunotherapy for Treatment of Malignancy," *Annual Review of Medicine* 52:125-145.

International Search Report mailed on May 21, 2008, for PCT Application No. PCT/US07/23620, filed on Nov. 8, 2007, 1 page.

Liang, T.W-Y. et al. (Apr. 2008). "TES7, a Monoclonal Antibody Targeting B7-H3, Potently Inhibits Hs-700T Growth in vivo," *The FASEB Journal* 22:Abstract 321.11, located at <http://www.fasebj.org/cgi/content/meeting_abstract/22/1_MeetingAbstracts/321.11?maxtoshow=&HITS=10&hits=10&RESULTFORMAT=&author1=liang&andorexacttitle=and&andorexacttitleabs=and&andorexactfulltext=and&searchid=1&FIRSTINDEX=0&sortspec=relevance&fdate=1/1/2008&resourcetype=HWCIT>, 1 page.

Written Opinion of the International Searching Authority mailed on May 21, 2008, for PCT Application No. PCT/US07/23620, filed on Nov. 8, 2007, 3 pages.

Dermer, G.B. (Mar. 1994). "Another Anniversary for the War on Cancer," *Bio/Technology* 12(3):320.

Lee, K.H. et al. (Dec. 1, 1999). "Increased Vaccine-Specific T Cell Frequency After Peptide-Based Vaccination Correlates with Increased Susceptibility to In Vitro Stimulation But Does Not Lead to Tumor Regression," *The Journal of Immunology* 163(11):6292-6300.

Zips, D. et al. (Jan.-Feb. 2005). "New Anticancer Agents: In Vitro and In Vivo Evaluation," *in vivo* 19(1):1-7.

\* cited by examiner

Western Blot
recombinant human B7H3 (4Ig) R&D

| | TES 7 | | 2nd AB only | |
|---|---|---|---|---|
| MW/kD | red | nr | red | nr |
| 222 — | | | | |
| 114 — | | | | |
| 79 — | |  | | |
| 49 — | | | | |
| 33 — | | | | |
| 27 — | | | | |
| 16 — | | | | |

FIGURE 11

```
TE87-VK    DVQITQSPSYLAASPGETITVNC RASESISKYLA WYQEKPGKTNKLLIY SGSTLQS GIPSRFSGSGSGSDFTLTISSLEPEDFAMYYC HQHNEFPLT FGAGTKLELK
AAK94808   DIQMTQSPSSLSASVGDRVTITC QASQDISNYLN WYQQKPGKAPKLLIY DASNLET GVPSRFSGSGSGTDFTFTISSLQPEDIATYYC QQYDDLPLT FGGGTKVEIK
TE87-HuVK1 -----------I----------- RASESISKYLA --------------- SGSTLQS ------------------------------- EQHNEFPLT ----------
TE87-HuVK2 -----------I----------- RASESISKYLA -------------M- SGSTLQS -----------------I------------- EQHNEFPLT ----------
```

FIGURE 12

```
TES7-VH     QVQLQQSGPELVKPGTSVRISCKASGYTFT SYYIH WVKQRPGQGLEWIG WIYPGNVNTKYNENFKG KATLTADKSSSTAYMQLSSLTSEDSAVYFCAR G     GYFFDQ WGQGTTLTVSS
AAA18279    QVQLVQSGAEVKKPGSSVKVSCKASGGTFS STAIS WVRQAPGQGLEWMG GIIPIFGTANYAQKFQG RVTITADKSTSTAYMELSSLRSEDTAVYYCAR GDILNGLNWFDP WGQGTLVTVSS
TES7-HuVH1  ----------------------------- Y--T SYYIH ------------- WIYPGNVNTKYNENFKG -A-------------- C     GYFFDQ -----------
TES7-HuVH2  ----------------------------- Y--T SYYIH -----------I- WIYPGNVNTKYNENFKG KA-L------------ G     GYFFDQ -----------
```

TES7 AND ANTIBODIES THAT BIND THERETO

TECHNICAL FIELD

This invention is in the fields of biology and immunotherapy. More specifically, it concerns a novel disease and cancer-associated antigen, TES7, and polyclonal and monoclonal antibodies and other polypeptides that bind to TES7. The invention further provides the diagnosis and/or treatment of a variety of human diseases and cancers associated with TES7 using antagonists, modulators and peptides that bind to TES7, including anti-TES7 antibodies.

BACKGROUND OF THE INVENTION

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments. See for example, *Cancer: Principles and Practice of Oncology*, 6$^{th}$ Edition (2001) Chapt. 20 pp. 495-508. These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are two examples of such therapeutics. Alternatively, antibodies can be used to make antibody conjugates where the antibody is linked to a toxic agent and directs that agent to the tumor by specifically binding to the tumor. Gemtuzumab ozogamicin is an example of an approved antibody conjugate used for the treatment of leukemia. Monoclonal antibodies that bind to cancer cells and have potential uses for diagnosis and therapy have been disclosed in publications. See, for example, the following patent applications which disclose, inter alia, some molecular weights of target proteins: U.S. Pat. No. 6,054,561 (200 kD c-erbB-2 (Her2), and other unknown antigens 40-200 KD in size) and U.S. Pat. No. 5,656,444 (50 kD and 55 kD oncofetal protein). Example of antibodies in clinical trials and/or approved for treatment of solid tumors include: Trastuzumab (antigen: 180 kD, HER2/neu), Edrecolomab (antigen: 40-50 kD, Ep-CAM), Anti-human milk fat globules (HMFG1) (antigen >200 kD, HMW Mucin), Cetuximab (antigens: 150 kD and 170 kD, EGF receptor), Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the level of expression or in access of or activity of the antibody at these sites.

Another type of immunotherapy is active immunotherapy, or vaccination, with an antigen present on a specific cancer(s) or a DNA construct that directs the expression of the antigen, which then evokes the immune response in the individual, i.e., to induce the individual to actively produce antibodies against their own cancer. Active immunization has not been used as often as passive immunotherapy or immunotoxins.

Several models of disease (including cancer) progression have been suggested. Theories range from causation by a single infective/transforming event to the evolution of an increasingly "disease-like" or 'cancer-like' tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up regulated and/or over-expressed in tumor tissues. In such situations, some researchers have suggested that the over-expression is linked to the acquisition of malignancy, while others suggest that the over-expression is merely a marker of a trend along a path to an increasing disease state.

In some cases, cancer targets, such as oncoproteins expressed or over-expressed in tumors, have been shown to be present during embryonic and fetal development and serve as a regulator of growth and differentiation. Some researchers have found that the expression of these oncoproteins during embryonic and fetal development appear to be restricted to specific tissues and also restricted to specific stages of development. In contrast, the expression of these oncoproteins in the adult has been shown to be associated with over-expression in tumor growth and/or a malfunction of tumor suppressor proteins.

An ideal diagnostic and/or therapeutic antibody would be specific for an antigen present on a large number of cancers, but absent or present only at low levels on any normal tissue. The discovery, characterization, and isolation of a novel antigen that is specifically associated with cancer(s) would be useful in many ways. First, the antigen could be used to make monoclonal antibodies against the antigen. An antibody would ideally have biological activity against cancer cells and be able to recruit the immune system's response to foreign antigens. An antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radio-isotope, a toxin, or a chemotherapeutic agent or liposome containing a chemotherapeutic agent, with the conjugated form being biologically active by virtue of the antibody directing the toxin to the antigen-containing cells.

One aspect desirable for an ideal diagnostic and/or therapeutic antibody is the discovery and characterization of an antigen that is associated with a variety of cancers. There are few antigens that are expressed on a number of types of cancer (e.g., "pan-cancer" antigen) that have limited expression on non-cancerous cells. The isolation and purification of such an antigen would be useful for making antibodies (e.g., diagnostic or therapeutic) targeting the antigen. An antibody binding to the "pan-cancer" antigen could be able to target a variety of cancers found in different tissues in contrast to an antibody against an antigen associated with only one specific type of cancer. The antigen would also be useful for drug discovery (e.g., small molecules) and for further characterization of cellular regulation, growth, and differentiation.

What is needed are novel targets on the surface of diseased and/or cancer cells that may be used to diagnose and treat such diseases and/or cancers with antibodies and other agents which specifically recognize the cell surface targets. There exists a further need, based on the discoveries disclosed herein, for novel antibodies and other agents which specifically recognize targets on the surface of cells that can modulate, either by reducing or enhancing, the disease-promoting activities of TES7. It is an object of this invention to identify modulators of TES7 that are capable of inhibiting its disease-associated activities. It is another object to provide novel compounds for use in the assay of TES7, and for use as immunogens or for selecting anti-human TES7 antibodies.

As described in detail below, the present inventors have discovered a novel antigen in the B7-H3 family of proteins, which we refer to herein as TES7. Similar polypeptides are known. See, for example, Sun et al., J. Immunol. 2002, 168: 6294-6297 which describes the identification of a mouse B7-H3 homolog, and characterizes the human B7-H3 gene as being shown to mediate T-cell proliferation and IFN-gamma production. Other antigen targets of novel antagonists, modulators and antibodies have also been described. For example, PCT Application WO 2004/001381 describes the novel antigen RAAG10 and antagonists, modulators and antibodies against this novel antigen target.

B7-H3 is a member of the human B7 family of proteins, a type I membrane protein with Ig-like domains. Originally identified with two Ig-like domains, other investigators have reported a four Ig-like domain form that is expressed on dendritic cells. Researchers have named the four Ig-like domain B7-H3, 4Ig-B7-H3 to distinguish it from the 2 Ig-like form. Neuroblastoma cells expressing 4Ig-B7-H3 treated with anti-4Ig-B7-H3 antibodies were more susceptible to NK cells. However, it is unclear that this activity can be attributed to only antibodies against the 4Ig-B7-H3 form because all reported antibodies raised against the 4Ig-B7-H3 also bound the two Ig-like form of B7H3 (Steinberger et al., J. Immunol. 2004, 172(4): 2352-2359 and Castriconi et al., PNAS 2004, 101(34): 12640-12645).

In addition to is expression on neuroblastomas, B7-H3 is also known to be expressed on a variety of cancer cells. The present inventors have discovered a novel antigen that we refer to herein as TES7, identified as the antigen target of the novel antagonists, modulators and antibodies provided herein.

SUMMARY OF THE INVENTION

The invention provides for TES7 antagonists, modulators, and monoclonal antibodies that bind to TES7, which is expressed on a variety of human cancers. In one aspect, the invention is a family of monoclonal antibodies that bind to TES7. TES7 shares characteristics with the 4Ig form of B7-H3.

In another aspect, the invention is a monoclonal antibody anti-TES7 that is produced by the host cell line Testis.1.2G7.1E11 deposited on Sep. 22, 2005 at the American Type Culture Collection with a Patent Deposit Designation of PTA-7093. In another aspect, the invention is a monoclonal antibody to the 4IG form of B7-H3 that is produced by the host cell line Stomach3.1E10.1G8 deposited on 8 Aug. 2007 at the American Type Culture Collection with a Patent Deposit Designation of PTA-8576.

In yet another aspect, the invention is a method of generating monoclonal antibody anti-TES7 reactive with diseased and/or cancerous cells comprising the steps of: (a) immunizing a host mammal with an immunogen; (b) obtaining lymphocytes from the mammal; (c) fusing lymphocytes (b) with a myeloma cell line to produce a hybridoma; (d) culturing the hybridoma of (c) to produce monoclonal antibodies; and (e) screening the antibodies to select only those antibodies which bind to diseased and/or cancerous cells or cell lines but do not bind to non-cancerous or normal cells or cell lines, or bind to normal cells at a lower level or in a different fashion.

In another aspect, the invention is a method of generating an anti-TES7 antibody comprising culturing a host cell encoding such antibody or progeny thereof under conditions that allow production of the antibody, and purifying the anti-TES7 antibody.

In another aspect, the invention provides methods of generating any of the antibodies (or polypeptides) described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the invention is an anti-TES7 antibody or a polypeptide (which may or may not be an antibody) that competitively inhibits preferential binding of an anti-TES7 antibody to TES7. In some embodiments, the invention is an antibody or a polypeptide (which may or may not be an antibody) that binds preferentially to the same or different epitope(s) on TES7 as other anti-TES7 antibodies.

In another aspect, the invention is a TES7 modulator (which may or may not be a polypeptide) that competitively inhibits preferential binding of an anti-TES7 antibody to TES7. In some embodiments, the invention can be a small molecule or chemical compound that binds preferentially to the same or different epitope(s) on TES7 as other anti-TES7 antibodies.

In yet another aspect, the invention is a composition comprising TES7 bound by an antibody specific for an epitope of TES7. In one embodiment, the antibody is anti-TES7. In other embodiments, two or more anti-TES7 antibodies are administered, with such antibodies mapping to two or more different epitopes on TES7. In some embodiments, the anti-TES7 antibody is linked to a therapeutic agent or a detectable label.

In another aspect, the invention is an antibody comprising a fragment or a region of an anti-TES7 antibody. In one embodiment, the fragment is a light chain of the antibody. In another embodiment, the fragment is a heavy chain of the antibody. In yet another embodiment, the fragment contains one or more variable regions from a light chain and/or a heavy chain of the antibody. In yet another embodiment, the fragment contains one or more complementarity determining regions (CDRs) from a light chain and/or a heavy chain of the antibody.

In another aspect, the invention provides polypeptides (which may or may not be antibodies) comprising any of the following: (a) one or more CDRs (or fragments thereof) from the light or heavy chain; (b) three CDRs from the light chain; (c) three CDRs from the heavy chain; (d) three CDRs from the light chain and three CDRs from the heavy chain; (e) the light chain variable region; (f) the heavy chain variable region of the anti-TES7 antibody.

In another aspect, the invention is a humanized antibody. In some embodiments, the humanized antibody comprises one or more CDRs of a non-human anti-TES7 antibody. In some embodiments, the humanized antibody binds to the same or different epitope(s) as other anti-TES7 antibodies. Generally, a humanized antibody of the invention comprises one or more (one, two, three, four, five, six or fragments thereof) CDRs which are the same and/or derived from the CDR(s) of the original non-human anti-TES7 antibody. In some embodiments, the human antibody binds to the same or different epitope(s) as other anti-TES7 antibodies. In another aspect, the invention is a chimeric antibody comprising variable regions derived from variable regions of a heavy chain and a light chain of a non-human anti-TES7 antibody and constant regions derived from constant regions of a heavy chain and a light chain of a human antibody.

In another aspect, the invention is an isolated polynucleotide that encodes an antibody mu-anti-TES7 that is produced by a host cell with a deposit number of ATCC 7093, or progeny thereof. This invention encompasses antibody polypeptides having the inherent binding or biological activities of any of the above-specified antibodies. In another aspect, the invention provides polynucleotides encoding any of the antibodies (including antibody fragments) as well as any other polypeptides described herein.

In another aspect, the invention is a pharmaceutical composition comprising any of the polypeptides (including any of the antibodies described herein) or polynucleotides described herein, such as pharmaceutical compositions comprising an anti-TES7 antibody linked to a chemotherapeutic agent, an antibody comprising a fragment of an anti-TES7 antibody, a humanized antibody of a non-human TES7 antibody, a chimeric antibody comprising variable regions derived from variable regions of a non-human anti-TES7 antibody and constant regions derived from a human antibody, or a human antibody with one or more properties of a non-human anti-TES7 antibody, or of the anti-TES7 antibody described herein linked to a chemotherapeutic agent (such as a radioactive moiety), and a pharmaceutically acceptable excipient.

In one aspect, the invention is a composition comprising an anti-TES7 antibody bound to TES7 present on a diseased or cancerous cell. In preferred embodiments, the cancer cell is selected from the group consisting of kidney, lung, and prostate cancer cells. In some embodiments, the cancer cell is isolated. In some embodiments, the cancer cell is in a biological sample. Generally, the biological sample is from an individual, such as a human.

In another aspect, the invention is a method of diagnosing disease in an individual by detecting TES7 on cells from the individual, particularly diseases or disorders associated with inflammatory or autoimmune responses in individuals. In other aspects of the invention, methods are provided for modulating inflammatory or autoimmune responses in individuals. Diseases and conditions resulting from inflammation and autoimmune disorders that may be subject to treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

In another aspect, the invention is a method for diagnosing whether an individual has cancer, comprising determining whether there is expression of TES7 on selected cells from the individual, wherein the expression of TES7 on said cells is indicative of said cancer. In some embodiments, the expression of TES7 is determined using an anti-TES7 antibody. In some embodiments, the method involves detecting the level of TES7 expression from cells. The term "detection" as used herein includes qualitative and/or quantitative detection (measuring levels) with or without reference to a control.

In yet another aspect, the invention is a method of diagnosing cancer in an individual by detecting TES7 on or released from cells from the individual, wherein the cancer is selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterior unveal melanoma, rare hematologic disorders, renal metastatic cancer, rhabdoid tumor, rhabdomyosarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In another aspect, the invention is a method for aiding diagnosis of cancer (such as but not limited to kidney, lung, or prostate cancer) in an individual comprising determining the expression of TES7 in a biological sample from the individual. In some embodiments, the expression of TES7 is determined using an anti-TES7 antibody. In some embodiments, the method is detecting the level of TES7 expression from cells. The TES7 released from the cancer may contribute to elevated levels of TES7 or a portion thereof, being detectable in body fluids (e.g., blood, salivary or gut mucinous secretions).

In yet another aspect, the invention is a method of treating cancer by administering an effective amount of an antibody that binds to TES7 sufficient to reduce growth of cancerous cells. In some embodiments, the antibody is an anti-TES7 antibody. In certain embodiments, the cancerous cells are selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, colon cancer, prostate cancer, lung cancer, sarcoma, renal metastatic cancer, thyroid metastatic cancer, and clear cell carcinoma.

In yet another aspect, the invention is a method of delaying development of metastasis in an individual having cancer comprising administering an effective amount of at least one of a family of antibodies that bind specifically to TES7. In one embodiment, the antibody is an anti-TES7 antibody. In another aspect, the invention is a method of inhibiting growth and/or proliferation of cancer cells in vitro or in an individual comprising administering an effective amount of a composition comprising an anti-TES7 antibody associated with (including linked to) a chemotherapeutic agent to the cell culture or sample, or to the individual.

In yet another aspect, the invention is a method of delivering a therapeutic agent to a cancerous cell in an individual by administering to the individual an effective amount of at least one member of a family of antibodies, which bind specifically to TES7. In other embodiments, an anti-TES7 antibody is delivered to an individual in combination with (including linked to) another therapeutic agent.

In some embodiments, the anti-TES7 antibody is a humanized antibody derived from a named antibody herein (generally, but not necessarily, comprising one or more partial or intact CDRs of the antibody). In some embodiments, the anti-TES7 antibody is a human antibody with one or more properties of the named antibody. In some embodiments, the chemotherapeutic agent (such as a toxin or a radioactive molecule) is delivered into the cancer cells (is internalized). In some embodiments, the agent is saporin.

In another aspect, the invention is a method of treating cancer in an individual comprising administering an effective amount of a composition comprising an anti-TES7 antibody associated with (including linked to) a chemotherapeutic agent to the individual.

The present invention further provides methods for modulating, either by enhancing or reducing, the association of TES7 with a cytoplasmic signaling partner. The association of TES7 with a cytoplasmic signaling partner can be impacted by contacting a TES7 molecule presenting on a cell surface, with an agent that modulates the binding of the signaling partner to TES7. Agents which block or reduce TES7 association with its binding and/or signaling partners can be used to modulate biological and pathological processes which are involved in TES7-mediated inflammation or immune responses. Pathological processes involving this action include tumor-associated cell growth.

Agents can be tested for their ability to block, reduce, enhance or otherwise modulate the association of TES7 with a binding partner, such as an anti-TES7 antibody. Specifically, an agent can be tested for the ability to modulate such an interaction by incubating a peptide comprising the TES7 interaction site (typically in its native conformation as it exists on intact living cells) with a binding partner and a test agent, and determining whether the test agent reduces or enhances the binding of the binding partner to the TES7 peptide.

Agonists, antagonists, and other modulators of TES7 function are expressly included within the scope of this invention. These agonists, antagonists and modulators are polypeptides that comprise one or more of the antigenic determinant sites in TES7, or comprise one or more fragments of such sites, variants of such sites, or peptidomimetics of such sites. These agonistic, antagonistic, and TES7 modulatory compounds are provided in linear or cyclized form, and optionally comprise at least one amino acid residue that is not commonly found in nature or at least one amide isostere. These compounds may be glycosylated. The agonists, antagonists, and other modulators of TES7 function of this invention are desirably used in all of the embodiments and methods described above with reference to antibodies.

Other aspects of this invention relate to the novel antigen identified and referred to herein as TES7. This antigen is suitable for use as an immunogen and for a variety of research, diagnostic and therapeutic purposes.

In certain aspects, the invention is a method for aiding in the diagnosis of disease in an individual comprising the steps of (i) assaying for the presence of TES7 in a blood or tissue sample obtained from an individual; (ii) detecting whether said sample has an increased amount of a TES7 marker relative to a normal (non-diseased) blood or tissue sample; and (iii) correlating an increased amount of said marker to a positive diagnosis or correlating the absence of an increased amount of said marker to a negative diagnosis for disease. In certain embodiments, the marker is detected using an anti-TES7 antibody. In certain embodiments, the method is effected by a technique selected from the group consisting of radionuclide imaging, flow cytometry, and immunohistochemistry.

BRIEF DESCRIPTION OF THE DRAWINGS

FIG. 11 shows variable light chain sequences of a murine anti-TES7 antibody (TES7-VK; SEQ ID NO:1) and two humanized variants, TES7-HuVK1 (SEQ ID NO:3) and TES7-HuVK2 (SEQ ID NO:4). CDR sequences are in orange. For the humanized versions, the proposed amino acids are the same as those presented in human sequence AAK94808 (SEQ ID NO:2) unless indicated otherwise.

FIG. 12 shows variable heavy chain sequences of a murine anti-TES7 antibody (TES7-VH; SEQ ID NO:5) and two humanized variants, TES7-HuVH1 (SEQ ID NO:7) and TES7-HuVH2 (SEQ ID NO:8). CDR sequences are in orange. For the humanized versions, the proposed amino acids are the same as those presented in human sequence AAA18279 (SEQ ID NO:6) unless indicated otherwise.

DETAILED DESCRIPTION OF THE INVENTION

Figure 1:
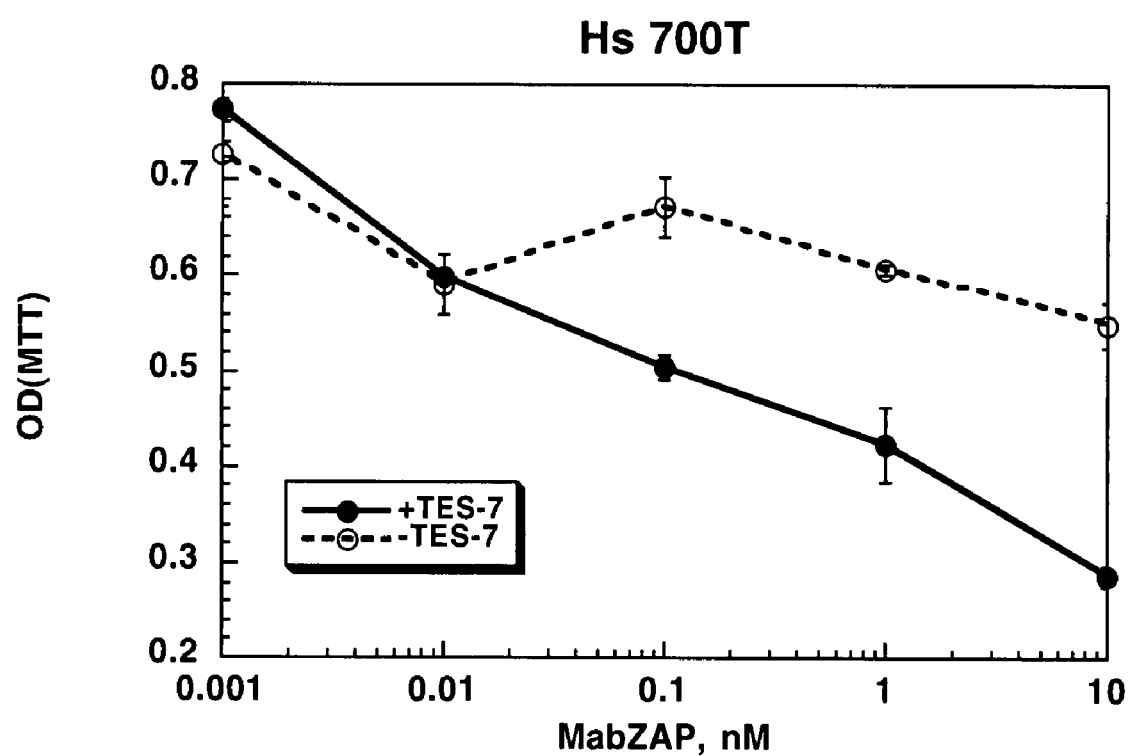
FIG. 1 shows the graphed results of the effect of mu-anti-TES7 and Mab-ZAP (an anti-IgG conjugated to saporin) on the growth of human pancreatic adenocarcinoma cell line Hs700T.

The invention provides a novel antigen, TES7, which is expressed on cancerous cells of various tissue origins, including but not limited to lung, prostate, and kidney cancers. Further, the invention provides monoclonal antibodies and polypeptides that bind to TES7 and methods making and using these antibodies and polypeptides to diagnose and treat various diseases human cancers associated with expression and/or over-expression of TES7.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

B7-H3 is a member of the human B7 family of proteins, a type I membrane protein with Ig-like domains. Originally B7-H3 was characterized as having two Ig-like domains, investigators have since reported a four Ig-like domain form of B7-H3 that is expressed on human dendritic cells. Researchers have named the four Ig-like domain 4Ig-B7-H3 to distinguish it from the 2Ig-like form. (Steinberger et al., J. Immunol. 2004, 172(4): 2352-2359 and Castriconi et al., PNAS 2004, 101(34): 12640-12645).

"TES7" refers to that novel antigen against which the antibodies of the present invention are directed, an antigen sharing characteristics of the 4Ig isoform of B7-H3. TES7 is a cell surface protein bound by anti-TES7 antibodies and present on normal human pancreas and liver tissue and several types of carcinomas. This antigen may have more than one different epitope, and epitopes may be non-linear. Several anti-B7-H3 antibodies are known to bind to non-linear epitopes, including some only present on the 4Ig isoform. It is currently believed that TES7 may be over-expressed in certain cancer cells in comparison to their normal tissue counterparts.

Agonists, antagonists, and other modulators of TES7 function are expressly included within the scope of this invention. These agonists, antagonists and modulators are polypeptides that comprise one or more of the antigenic determinant sites in TES7, or comprise one or more fragments of such sites, variants of such sites, or peptidomimetics of such sites. These agonistic, antagonistic, and TES7 modulatory compounds are provided in linear or cyclized form, and optionally comprise at least one amino acid residue that is not commonly found in nature or at least one amide isostere. These compounds may be glycosylated.

More specifically, the terms "TES7 modulator" as used herein are defined as any compound that (1) is capable of disrupting or blocking the interaction between human TES7 and its native ligands or an anti-TES7 antibody; (2) is capable of binding to human TES7 and its native ligands or an anti-TES7 antibody; (3) contains an antigenic site that can be used in the raising of antibodies capable of binding to human TES7 and its native ligands or an anti-TES7 antibody; (4) contains an antigenic site that can be used in the screening of antibodies capable of binding to human TES7 and its native ligands or an anti-TES7 antibody; (5) contains an antigenic site that an be used in the raising of antibodies capable of disrupting or blocking the interaction between human TES7 and its native ligands or an anti-TES7 antibody; (6) contains an antigenic site that can be used in the screening of antibodies capable of disrupting or blocking the interaction between human TES7 and its native ligands or an anti-TES7 antibody. TES7 modulators may be "TES7 agonists" or "TES7 antagonists" depending on whether their activity enhances or inhibits normal TES7 biological activity, respectively.

TES7 agonists, antagonists and modulators include TES7 variants, TES7 peptide antagonists, peptidomimetics, and small molecules, anti-TES7 antibodies and immunoglobulin variants, amino acid variants of human TES7 including amino acid substitution, deletion, and addition variants, or any combination thereof, and chimeric immunoglobulins. The TES7 agonists, antagonists and modulators of this invention are based on the inventors' identification of the TES7 domains involved in the binding of human TES7 to its native ligands or anti-TES7 antibodies. Thus, the invention provides TES7 agonists, antagonists and modulators with molecular structures that duplicate or mimic one or more of the anti-TES7 binding domains of human TES7.

As used herein, the term "TES7 variant" denotes any amino acid variant of human TES7, including amino acid substitution, deletion, and addition variants, or any combination thereof. The definition encompasses chimeric molecules such as human TES7/non-human chimeras and other hybrid molecules. Also included in the definition is any fragment of a TES7 variant molecule that comprises the variant or hybrid region(s) of the molecule.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody".

"Humanized" antibodies refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al., (1989) Proc Natl Acad Sci USA 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K., et al., (1993) Cancer Res 53:851-856. Riechmann, L., et al., (1988) Nature 332:323-327; Verhoeyen, M., et al., (1988) Science 239:1534-1536; Kettleborough, C. A., et al., (1991) Protein Engineering 4:773-3783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S., et al., (1991) Proc Natl Acad Sci USA 88:2869-2873; Carter, P., et al., (1992) Proc Natl Acad Sci USA 89:4285-4289; and Co, M. S. et al., (1992) J Immunol 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a TES7 epitope is an antibody that binds this TES7 epitope with greater affinity, avidity, more readily, and/or with greater duration than it binds to other TES7 epitopes or non-TES7 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The term "immunologically active" in reference to an epitope being or "remaining immunologically active" refers to the ability of an antibody (e.g., anti-TES7 antibody) to bind to the epitope under different conditions, for example, after the epitope has been subjected to reducing and denaturing conditions.

Different biological functions are associated with anti-TES7 antibodies, including, but not limited to, ability to bind to TES7 (including TES7 on cancer cells, including but not limited to kidney, prostate, or lung, cancer cells); ability to bind to a portion of TES7 that is exposed on the surface of a living cell in vitro or in vivo; ability to deliver a chemotherapeutic agent to cancerous cells (such as kidney, prostate, or lung cancer cells) expressing TES7; ability to deliver a therapeutic agent or detectable marker into cancer cells expressing TES7. As discussed herein, polypeptides (including antibodies) of the invention may have any one or more of these characteristics.

An "anti-TES7 equivalent antibody" or "anti-TES7 equivalent polypeptide" refers to an antibody or a polypeptide having one or more biological functions associated with an anti-TES7 antibody, such as, for example binding specificity.

As used herein, "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

Agents that are employed in the methods of this invention can be randomly selected or rationally selected or designed. As used herein, an agent is said to be randomly selected when the agent is chosen randomly without considering the specific sequences involved in the association of TES7 with its native binding partners or known antibodies. An example of randomly selected agents is the use of a chemical library or a peptide combinatorial library.

As used herein, an agent is said to be rationally selected or designed when the agent is chosen on a nonrandom basis that takes into account the sequence of the target site and/or its conformation in connection with the agent's action. With respect to anti-TES7 agents, it is currently believed that there are at least three epitopes on TES7 against which antibodies can be raised and therefore at least three sites of action for agents that block TES7/anti-TES7 interaction. This invention also encompasses agents that act at the sites of interaction between TES7 and its native binding partner, although other ligands and their active TES7-interactive sites are also encompassed within the scope of this invention, whether currently known or later identified. Agents can be rationally selected or rationally designed by utilizing the peptide sequences that make up the contact sites of the receptor/ligand and/or TES7/anti-TES7 antibody complex. For example, a rationally selected peptide agent can be a peptide whose amino acid sequence is identical to an epitope appearing on TES7 as it is exposed on the surface of a living cell in its native environment. Such an agent will reduce or block the association of the anti-TES7 antibody with TES7, or the association of TES7 with its native ligand, as desired, by binding to the anti-TES7 antibody or to the native ligand.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE)) to the antibody, as well as indirect labeling of the probe or antibody by reactivity with a detectable substance.

As used herein, the term "association", with regard to the antibody, includes covalent and non-covalent attachment or binding to an agent (e.g., chemotherapeutic agent). The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

A "biological sample" encompasses a variety of sample types obtained from an individual and can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

An "effective amount" of a pharmaceutical composition, in one embodiment, is an amount sufficient to effect beneficial or desired results including, without limitation, clinical results such as shrinking the size of the tumor (in the cancer context, for example, breast or prostate cancer), retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) cancerous cells and to reduce and/or delay the development, or growth, of metastases of cancerous cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages comprise 0.1- to 100 mg/kg/body weight. The preferred dosages comprise 1- to 100-mg/kg/body weight. The most preferred dosages comprise 10- to 100-mg/kg/body weight.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. from its original source.

An "individual" is a vertebrate, preferably a mammal, more preferably a human. Mammals include, but are not limited to, farm animals, sport animals, pets, primates, mice and rats.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

Also encompassed within the scope of the invention are peptidomimetics of the TES7 peptide agonists, antagonists and modulators (including anti-TES7 antibodies) described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond (—C(.dbd.O)—NH—) in a TES7 peptide agonist, antagonist or modulators with an amide isostere. Suitable amide isosteres include —CH$_2$-NH—, —CH$_2$-S—, —CH$_2$-S(O)$_n$- (where n is 1 or 2), —CH$_2$-CH$_2$-, —CH.db-d.CH— (E or Z), —C(.dbd.O)—CH$_2$-, —CH(CN)—NH—, —C(OH)—CH$_2$-, and —O—C(.dbd.O)—NH—. The amide bonds in a TES7 peptide agonist, antagonist or modulator that are suitable candidates for replacement with amide isosteres include bonds that are hydrolyzable by the endogenous esterases or proteases of the intended subject of TES7 peptide agonist, antagonist or modulator treatment.

As used herein, "substantially pure" refers to material that is at least 50% pure (i.e., free from contaminants), more preferably at least 90% pure, more preferably at least 95% pure, more preferably at least 98% pure, more preferably at least 99% pure, or greater, pure.

"Toxin" refers to any substance, which effects an adverse response within a cell. For example, a toxin directed to a cancerous cell would have an adverse, sometimes deleterious effect, on the cancerous cell. Examples of toxins include, but are not limited to, radioisotopes, calicheamicin, and maytansinoids.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

III. Methods of Making Antibodies and Polypeptides

Methods of making monoclonal antibodies are known in the art. One method which may be employed is the method of Kohler and Milstein, Nature 256:495-497 (1975) or a modification thereof. Typically, monoclonal antibodies are developed in non-human species, such as mice. In general, a mouse or rat is used for immunization but other animals may also be used. The antibodies are produced by immunizing mice with an immunogenic amount of cells, cell extracts, or protein preparations that contain human TES7. The immunogen can be, but is not limited to, primary cells, cultured cell lines, cancerous cells, nucleic acids, or tissue. In one embodiment, human lung carcinoma cells are used. Cell lines that are suitable for immunization are detailed in Example 1. Cells used for immunization, for example, human testis or pancreatic adenocarcinoma or stomach cells, may be cultured for a period of time (at least 24 hours) prior to their use as an immunogen. Cells (e.g., human testis, stomach, or pancreatic adenocarcinoma cells) may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi-weekly, or weekly, or may be administered in such a way as to maintain viability in the animal (e.g., in a tissue recombinant). Example 2 describes methods used to generate anti-TES7 antibodies and may be used to generate other monoclonal antibodies, which bind to TES7.

In one embodiment, monoclonal antibodies that bind to TES7 are obtained by using host cells that over-express TES7 as an immunogen. Such cells include, by way of example and not by limitation, human lung carcinoma cells and human colon cancer cells.

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen (e.g., surface of human fetal kidney cells, surface of cancer cell lines, TES7, fetal bladder sections, etc.) using FACS or immunohistochemistry (IHC screening). The selected monoclonal antibody-secreting hybridomas are then cultured either in vitro (e.g., in tissue culture bottles or hollow fiber reactors), or in vivo (e.g., as ascites in mice). Example 3 provides further details about the methods utilized to obtain and screen an anti-TES7 antibody.

As another alternative to the cell fusion technique, EBV immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, monoclonal antibody anti-TES7 and any other equivalent antibodies can be sequenced and produced recombinantly by any means known in the art (e.g., humanization, use of transgenic mice to produce fully human antibodies, phage display technology, etc.). In one embodiment, anti-TES7 monoclonal antibody is sequenced and the polynucleotide sequence is then cloned into a vector for expression or propagation. The sequence encoding the antibody of interest may be maintained in a vector in a host cell and the host cell can then be expanded and frozen for future use.

The polynucleotide sequence of monoclonal antibody anti-TES7 and any other equivalent antibodies may be used for genetic manipulation to generate a "humanized" antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; and 6,331,415.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J. Immunol.* 138: 4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al., *Nucl. Acids Res.,* 19:2471-2476 (1991) and in U.S. Pat. Nos. 6,180,377; 6,054,297; 5,997,867; and 5,866, 692.

The invention also encompasses single chain variable region fragments ("scFv") of antibodies of this invention, such as mu-anti-TES7. Single chain variable region fragments are made by linking light and/or heavy chain variable regions by using a short linking peptide. Bird et al. (1988) *Science* 242: 423-426 describes example of linking peptides which bridge approximately 3.5 nm between the carboxy terminus of one variable region and the amino terminus of the other variable region. Linkers of other sequences have been designed and used, Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to TES7 agonists, antagonists, modulators and antibodies, including functionally equivalent antibodies and polypeptides that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the polypeptides and antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of an antibody produced from a hybridoma deposited with the ATCC as described herein. For purposes of this invention, an antibody fusion protein contains one or more anti-TES7 polypeptides and another amino acid sequence to which it is not attached in the native molecule, for example, a heterologous sequence or a homologous sequence from another region.

An anti-TES7 polypeptide, and other TES7 agonists, antagonists and modulators can be created by methods known in the art, for example, synthetically or recombinantly. One method of producing TES7 peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see Kelley, R. F. & Winkler, M. E. in Genetic Engineering Principles and Methods, Setlow, J. K., ed., Plenum Press, N.Y., vol. 12, pp 1-19 (1990); Stewart, J. M. & Young, J. D. Solid Phase Peptide Synthesis Pierce Chemical Co. Rockford, Ill. (1984); see also U.S. Pat. Nos. 4,105,603; 3,972,859; 3,842,067; and 3,862,925).

Polypeptides of the invention may be conveniently prepared using solid phase peptide synthesis (Merrifield, J. Am. Chem. Soc., 85:2149 (1964); Houghten, Proc. Natl. Acad. Sci. USA 82:5132 (1985)).

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Methods for expressing antibodies recombinantly in plants or milk have been disclosed. See, for example, Peeters, et al. (2001) *Vaccine* 19:2756; Lonberg, N. and D. Huszar (1995) *Int. Rev. Immunol* 13:65; and Pollock, et al. (1999) *J Immunol Methods* 231:147. Methods for making derivatives of antibodies, e.g., humanized, single chain, etc. are known in the art. In another alternative, antibodies may be made recombinantly by phage display technology. See, for example, U.S. Pat. Nos. 5,565,332; 5,580,717; 5,733,743; 6,265,150; and Winter et al., *Annu. Rev. Immunol.* 12:433-455 (1994).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified TES7 or portions thereof for cells expressing the antibody or protein of interest. The "panning" procedure is conducted by obtaining a cDNA library from tissues or cells that express the antibody or protein of interest, over-expressing the cDNAs in a second cell type, and screening the transfected cells of the second cell type for a specific binding to TES7. Detailed descriptions of the methods used in cloning mammalian genes coding for cell surface proteins by "panning" can be found in the art. See, for example, Aruffo, A. and Seed, B. *Proc. Natl. Acad. Sci. USA*, 84, 8573-8577 (1987) and Stephan, J. et al., *Endocrinology* 140: 5841-5854 (1999).

cDNAs encoding anti-TES7 antibodies, and other TES7 peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to TES7 is effected by an immunoassay or FACS. A cell over-expressing the antibody or protein of interest can be identified.

Various techniques are also available which may now be employed to produce mutant TES7 peptide agonists, antagonists, and modulators which encodes for additions, deletions, or changes in amino acid sequence of the resultant protein relative to the parent TES7 peptide agonist, antagonist or modulator molecule.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-TES7 polypeptide could be produced by an automated polypeptide synthesizer employing the solid phase method.

IV. Methods for Screening Polypeptides and Monoclonal Antibodies

Several methods may be used to screen polypeptides and monoclonal antibodies that bind to TES7. It is understood that "binding" refers to biologically or immunologically relevant binding, i.e., binding which is specific for the unique antigen for which the immunoglobulin molecule is encoded, or to which the polypeptide is directed. It does not refer to nonspecific binding that may occur when an immunoglobulin is used at a very high concentration against a non-specific target. In one embodiment, monoclonal antibodies are screened for binding to TES7 using standard screening techniques. In this manner, anti-TES7 monoclonal antibody was obtained. In accordance with the Budapest Treaty, a hybridoma which produces anti-TES7 monoclonal antibodies has been deposited in the American Type Culture Collection (ATCC) 10801 University Blvd., Manassas Va. 20110-2209 on Sep. 22, 2005 with a Patent Deposit Designation of PTA# 7093.

Monoclonal antibodies that bind to TES7 are screened for binding to cancerous tissues and non-cancerous cells. In one embodiment, monoclonal antibodies which bind to TES7 and that are also cross reactive to human cancerous cells or tissues, but not to normal cells or tissues to the same degree, are selected. One method that may be employed for screening is immunohistochemistry (IHC). Standard immunohistochemical techniques are known to those of average skill in the art. See, for example, *Animal Cell Culture Methods* (J. P. Mather and D. Barnes, eds., Academic Press, Vol. 57, Ch. 18 and 19, pp. 314-350, 1998). Biological samples (e.g., tissues) may be obtained from biopsies, autopsies, or necropsies. To ascertain if TES7 is present only on cancerous cells, anti-TES7 antibodies may be used to detect the presence of TES7 on tissues from individuals with cancer while other non-cancerous tissues from the individual suffering from cancer or tissues from individuals without cancer are used as a control. The tissue can be embedded in a solid or semi-solid substance that prevents damage during freezing (e.g., agarose gel or OCT) and then sectioned for staining. Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include but are not limited to carcinomas, adenocarcinomas, sarcomas, adenosarcomas, lymphomas, and leukemias.

In yet another alternative, cancerous cells lines such as HMEC (BioWhittaker CC-2251), HUVEC (Primary endothelial cells), BT-474 (ATCC# HTB-20), MCF7 (ATCC# HTB22), MDA-MB-175-VII (ATCC# HB-25), MDA-MB-361 (ATCC# HB-27), SKBR3 (ATCC# HTB-30), 9979 (Raven proprietary lung cancer cell line), A549 (ATCC# CCL-185), CA130 (Raven proprietary lung small cell carcinoma cell line), Calu-3 (ATCC# HTB-55), SKMES-1 (ATCC# HTB-58), ES-2 (ATCC# CRL-1978), SKOV3 (ATCC# HTB-77), 9926 (Raven proprietary pancreatic adenocarcinoma cell line), AsPC-1 (ATCC# CRL-1682), HPAF-11 (ATCC# CRL-1997), Hs700T (ATCC# HTB-174), Colo205 (ATCC# CCL-222), HT-29 (ATCC# HTB-38), SW480 (ATCC# CCL-228), SW948 (ATCC# CCL-237), 293 (ATCC # CRL-1573), 786-0 (ATCC# CRL-1932), A498 (ATCC# HTB-44), Caki-2 (ATCC# HTB-47), COS-7 (ATCC# CRL-1651), RL-65 (ATCC # CRL-10345), SV-T2 (ATCC# CCL-163.1), 22RV1 (ATCC# CRL-2505), DU145 (ATCC# HTB-81), LNCaP (ATCC# CRL-1740), PC-3 (ATCC# CRL-1435), TDH (Raven proprietary prostate cancer cell line), Hs746T (ATCC# HTB-135), NCI-N87 (ATCC# CRL-5822) and normal cells from their respective tissues may be used to screen for monoclonal antibodies which are specific for cancerous tissue. Primary, or low passage, cell cultures derived from normal tissues from different organs, including but not limited to, kidney, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™, as described in WO 01/43869, and screened for the binding of antibody using IHC as described above for tissues. Alternatively, cells may be removed from the growth surface using non-proteolytic means and spun into a pellet, which is then embedded and treated as tissues for IHC analysis as described above. Cells may be inoculated into immunodeficient animals, a tumor allowed to grow, and then this tumor may be harvested, embedded, and used as a tissue source for IHC analysis. In another alternative, single cells may be screened by incubating with the primary antibody, a secondary "reporter" antibody linked to a fluorescent molecule and then analyzed using a fluorescent activated cell-sorting (FACS) machine.

Several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA. PolyMICA (polyclonal Mirror Image Complementary Antibodies) technique, described by D. C. Mangham and P. G. Isaacson (*Histopathology* (1999) 35(2):129-33), can be used to test binding of primary antibodies (e.g., anti-TES7 antibodies) to normal and cancerous tissue. Several kinds of polyMICA™ Detection kits are commercially available from The Binding Site Limited (P.O. Box 4073 Birmingham B29 6AT England). Product No. HK004.D is a polyMICA™ Detection kit which uses DAB chromagen. Product No. HK004.A is a polyMICA™ Detection kit which uses AEC chromagen. Alternatively, the primary antibody may be directly labeled with the detectable marker.

The first step in IHC screening to select for an appropriate antibody is the binding of primary antibodies raised in mice (e.g., anti-TES7 antibodies) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art. See, for example, Stephan et al. *Dev. Biol.* 212: 264-277 (1999), and Stephan et al. *Endocrinology* 140: 5841-54 (1999).

V. Methods of Characterizing Anti-TES7 Antibodies

Several methods can be used to characterize anti-TES7 antibodies. One method is to identify the epitope to which it binds. Epitope mapping is commercially available from various sources, for example, Pepscan Systems (Edelhertweg 15, 8219 PH Lelystad, The Netherlands). Epitope mapping can be used to determine the sequence to which an anti-TES7 antibody binds. The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with anti-TES7 antibody. The epitope to which anti-TES7 antibody binds can be determined in a systematic screening by using overlapping peptides derived from the extracellular sequence and determining binding by anti-TES7 antibody.

Yet another method that can be used to characterize an anti-TES7 antibody is to use competition assays with other antibodies known to bind to the same antigen, i.e., TES7 to determine if anti-TES7 antibodies binds to the same epitope as other antibodies. Examples of commercially available antibodies to TES7 may be available and may be identified using the binding assays taught herein. Competition assays are well known to those of skill in the art, and such procedures and illustrative data are detailed further in the Examples. Anti-TES7 antibodies can be further characterized by the tissues, type of cancer or type of tumor to which they bind.

Another method of characterizing anti-TES7 antibodies is by the antigen to which it binds. Anti-TES7 antibodies were used in Western blots with cell lysates from various human cancers. As is known to one of skill in the art, Western blotting can involve running cell lysates and/or cell fractions on a denaturing or non-denaturing gel, transferring the proteins to nitrocellulose paper, and then probing the blot with an antibody (e.g., anti-TES7 antibody) to see which proteins are bound by the antibody. This procedure is detailed further in Example 4. TES7 is associated with various human cancers of different tissues including, but not limited to colon, breast, ovary, pancreas and lung. Further description of TES7 is given in Examples 5 and 6.

VI. Methods of Diagnosing Cancer Using Anti-TES7 Antibodies and TES7 Modulators

Monoclonal antibodies to TES7 made by the methods disclosed herein may be used to identify the presence or absence of cancerous cells in a variety of tissues, including but not limited to, ovary, breast, lung, prostate, colon, kidney, pancreas, skin, thyroid, brain, heart, liver, stomach, nerve, blood vessels, bone, and upper digestive tract, for purposes of diagnosis. Monoclonal antibodies to TES7 made by the methods disclosed herein may also be used to identify the presence or absence of cancerous cells, or the level thereof, which are circulating in blood after their release from a solid tumor. Such circulating antigen may be an intact TES7 antigen, or a fragment thereof that retains the ability to be detected according to the methods taught herein. Such detection may be effected by FACS analysis using standard methods commonly used in the art.

These uses can involve the formation of a complex between TES7 and an antibody that binds specifically to TES7. Examples of such antibodies include but are not limited to those anti-TES7 monoclonal antibodies produced by the hybridoma deposited in the ATCC with the designation PTA# 7093. The formation of such a complex can be in vitro or in vivo. Without being bound by theory, monoclonal antibody anti-TES7 can bind to TES7 through the extracellular domain of TES7 and may then be internalized.

In a preferred embodiment of the diagnostic methods of this invention, the antibody bears a detectable label. Examples of labels that may be used include a radioactive agent or a fluorophore, such as fluoroisothiocyanate or phycoerythrin.

As with other known antibodies used commercially for diagnostic and therapeutic purposes, the target antigen of this invention is broadly expressed in normal tissue. It is also up regulated in some tumors. Therefore, the particular dosages and routes of delivery of the antibodies of this invention as used for diagnostic or therapeutic agents will be tailored to the particular tumor or disease state at hand, as well as to the particular individual being treated.

One method of using the antibodies for diagnosis is in vivo tumor imaging by linking the antibody to a radioactive or radioopaque agent, administering the antibody to the individual and using an x-ray or other imaging machine to visualize the localization of the labeled antibody at the surface of cancer cells expressing the antigen. The antibody is administered at a concentration that promotes binding at physiological conditions.

In vitro techniques for detection of TES7 are routine in the art and include enzyme linked immunosorbent assays (ELISAs), immunoprecipitations, immunofluorescence, enzyme immunoassay (EIA), radioimmunoassay (RIA), and Western blot analysis.

In aspects of this invention, methods of radioimaging of tumors or neoplasms, or of measuring the effectiveness of a method of treatment with a radiolabelled antibody, comprising the step of administering a radiolabelled, tumor-specific antibody to an individual following the practice of this invention. The radiolabelled antibody may be a monoclonal or polyclonal antibody comprising a radiolabel, preferably selected from the group consisting of Technetium-99m, Indium-111, Iodine-131, Rhenium-186, Rhenium-188, Samarium-153, Lutetium-177, Copper-64, Scandium-47, Yttrium-90. Monoclonal antibodies labeled with therapeutic radionuclides such as Iodine-131, Rhenium-188, Holmium-166, Samarium-153 and Scandium-47, which do not compromise the immunoreactivity of antibodies and are not broken down in vivo, are especially preferred. The person skilled in the art will appreciate that other radioactive isotopes are known, and may be suitable for specific applications. The radioimaging may be conducted using Single Photon Emission Computer Tomography (SPECT), Position Emission Tomography (PET), Computer Tomography (CT) or Magnetic Resonance Imaging (MRI). Correlative imaging, which permits greater anatomical definition of location of metastases located by radioimmunoimaging, is also contemplated.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify cancerous cells at different stages of development. The antibodies may also be used to determine which individuals' tumors express the antigen on their surface at a pre-determined level and are thus candidates for immunotherapy using antibodies directed against said antigen. The antibodies may recognize both primary and metastasizing cancers of the kidney, ovary, prostate and pancreas and primary cancers of the lung that express TES7. As used herein, detection may include qualitative and/or quantitative detection and may include comparing the level measured to a normal cell for an increased level of expression of TES7 in cancerous cells.

The invention also provides methods of aiding diagnosis of cancer (such as but not limited to prostate, lung or kidney cancer) in an individual using any antibody that binds to TES7 and any other methods that can be used determine the level of TES7 expression. As used herein, methods for "aiding diagnosis" means that these methods assist in making a clinical determination regarding the classification, or nature, of cancer, and may or may not be conclusive with respect to the definitive diagnosis. Accordingly, a method of aiding diagnosis of cancer can comprise the step of detecting the level of TES7 in a biological sample from the individual and/or determining the level of TES7 expression in the sample. Antibodies recognizing the antigen or a portion thereof may also be used to create diagnostic immunoassays for detecting antigen released or secreted from living or dying cancer cells in bodily fluids, including but not limited to, blood, saliva, urine, pulmonary fluid, or ascites fluid.

Not all cells in a particular tumor of interest will express TES7, and cancerous cells in other tissues may express TES7, thus an individual should be screened for the presence or absence of TES7 on cancerous cells to determine the usefulness of immunotherapy in the individual. The anti-TES7 antibodies made by the methods disclosed herein may be used to determine whether an individual diagnosed with cancer may be deemed a candidate for immunotherapy using antibodies directed against TES7. In one embodiment, a cancerous tumor or a biopsy sample may be tested for expression of TES7, using antibodies directed against TES7. Individuals with cancer cells that express TES7 are suitable candidates for immunotherapy using antibodies directed against TES7. Staining with anti-TES7 antibody may also be used to distinguish cancerous tissues from normal tissues.

Methods of using anti-TES7 antibodies for diagnostic purposes are useful both before and after any form of anti-cancer treatment, e.g., chemotherapy or radiation therapy, to determine which tumors are most likely to respond to a given treatment, prognosis for individual with cancer, tumor subtype or origin of metastatic disease, and progression of the disease or response to treatment.

The compositions of this invention are also suitable for diagnosis of disease states other than cancer, using the methods generally described above in application with other diseased (non-cancerous) cells. Disease states suitable for use in the methods of this invention include, but are not limited to, diseases or disorders associated with inflammatory or autoimmune responses in individuals. The methods described above may be used for modulating inflammatory or autoimmune responses in individuals. Diseases and conditions resulting from inflammation and autoimmune disorders that may be subject to diagnosis and/or treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for diagnostic and/or therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

Uses described anywhere in this application for anti-TES7 antibodies also encompass the use of other TES7 agonists, antagonists and modulators as described herein. In such embodiments, the TES7 agonist, antagonist or other non-antibody modulator is substituted for the TES7 antibody in the steps described, and alterations within the scope of the ordinarily skilled practitioner are made to tailor the method to the substituted TES7 modulatory composition.

Monoclonal antibodies to TES7 made by the methods disclosed herein may be used to identify the presence or absence of human cancer stem cells in a variety of tissues. Cancer stem cells (CSCs) have been hypothesized to play a role in tumor growth and metastasis. Under this hypothesis, the CSCs provide a small, distinct subset of cells within each tumor that are capable of indefinite self-renewal and of developing into the more adult tumor cell(s) that are relatively limited in replication capacity. It has been hypothesized that these cancer stem cells might be more resistant to chemotherapeutic agents, radiation or other toxic conditions, and thus, persist after clinical therapies and later grow into secondary tumors, metastases or be responsible for relapse. It has been suggested that CSCs can arise either from 'normal' tissue stem cells or from more differentiated tissue progenitor cells. While supporting data for this hypothesis is strong for hematopoietic stem and progenitor cells and hematopoietic tumors, less is known about solid tumors and their respective CSCs.

Human cancer stem cells have several defining characteristics. Such characteristics are described in U.S. patent application Ser. No. 60/972,613 and are hereby incorporated by reference. Monoclonal antibodies to cell surface targets on cancer stem cells can be used to identify the presence or absence of cancer stem cells in a variety of tissues. Examples of TES7 expression on a variety of cancer stem cells are shown in Example 8 below. Monoclonal antibodies to TES7 made by the methods disclosed herein may also be used to identify the presence or absence of cancer stem cells, or the level of cancer stem cells in a sample or tissue or in circulation after their release from a solid tumor. Such circulating antigen may be an intact TES7 antigen, or a fragment thereof that retains the ability to be detected according to the methods taught herein. Such detection may be effected by FACS analysis using standard methods commonly used in the art. In another embodiment, such detection may be effected by immunohistochemical analysis of tissue samples using standard methods commonly used in the art.

These uses can involve the formation of a complex between TES7 and an antibody that binds specifically to TES7 on cancer stem cells. Examples of such antibodies include but are not limited to those anti-TES7 monoclonal antibodies produced by the hybridoma deposited in the ATCC with the designation PTA# 7093. The formation of such a complex can be in vitro or in vivo.

Uses described in this application that recite their use for anti-TES7 antibodies also encompass the use of other TES7 agonists, antagonists and modulators as described herein for the use of identification and treatment of cancer stem cells. In such embodiments, anti-TES7 antibodies and other TES7 agonists, antagonists and modulators are used for identification, diagnosis or therapeutic treatment of cancer stem cells using similar methods described, and alterations within the scope of the ordinary skilled practitioner are made to tailor the method to the identification/diagnosis or treatment of cancer stem cells.

VII. Compositions of this Invention

This invention also encompasses compositions, including pharmaceutical compositions, comprising anti-TES7 antibodies, polypeptides derived from anti-TES7 antibodies, polynucleotides comprising sequence encoding anti-TES7 antibodies, and other agents as described herein. As used herein, compositions further comprises one or more antibodies, polypeptides and/or proteins that bind to TES7, TES7 agonists, antagonists, modulators, and/or one or more polynucleotides comprising sequences encoding one or more antibodies, polypeptides and proteins that bind to TES7.

The invention further provides for conjugates of any TES7 peptide agonist, antagonist or modulator, and additional chemical structures that support the intended function or functions of the particular TES7 peptide agonist, antagonist or modulator. These conjugates include TES7 peptide agonist, antagonist or modulator covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (eds) Affinity Chromatography: A Practical Approach, IRL Press (1985); Lowe, "An Introduction to Affinity Chromatography", in Work et al. (eds) Laboratory Techniques in Biochemistry and Molecular Biology, Vol. 7, Part II, North-Holland (1979); Porath et al., "Biospecific Affinity Chromatography", in Neurath et al. (eds), The Proteins, 3rd ed., Vol. 1, pp. 95-178 (1975); and Schott, Affinity Chromatography, Dekker (1984).

Also provided herein are conjugates of TES7 peptide agonist, antagonist or modulator and any reporter moiety used in the diagnostic procedures discussed herein.

The TES7 peptide agonist, antagonist or modulator agents, polypeptides and proteins of this invention, including anti-TES7 antibodies, are further identified and characterized by any (one or more) of the following criteria: (a) ability to bind to TES7 (including TES7 on cancer cells, including but not limited to prostate, lung, or kidney cancer cells); (b) ability to competitively inhibits preferential binding of a known anti-TES7 antibody to TES7, including the ability to preferentially bind to the same TES7 epitope to which the original antibody preferentially binds; (c) ability to bind to a portion of TES7 that is exposed on the surface of a living cell in vitro or in vivo; (d) ability to bind to a portion of TES7 that is exposed on the surface of living cancer cells, such as but not limited to prostate, lung or kidney cancer cells; (e) ability to deliver a chemotherapeutic agent or detectable marker to cancerous cells (such as but not limited to prostate, lung, or kidney cancer cells) expressing TES7; (f) ability to deliver a therapeutic agent into cancerous cells (such as but not limited to prostate cancer cells) expressing TES7.

In some embodiments, the antibody of the invention is an antibody that is produced by a host cell with a deposit number of ATCC No. PTA# 7093, or progeny thereof. The present invention also encompasses various formulations of antibodies produced by these deposited hybridomas and equivalent antibodies or polypeptide fragments (e.g., Fab, Fab', F(ab')$_2$, Fv, Fc, etc.), chimeric antibodies, single chain (ScFv), mutants thereof, fusion proteins comprising an antibody portion, humanized antibodies, and any other modified configuration of any of these or equivalent antibodies that comprises an antigen (TES7), recognition site of the required specificity. The invention also provides human antibodies displaying one or more of the biological characteristics of an anti-TES7 family member. The equivalent antibodies of the anti-TES7 family (including humanized antibodies and human antibodies), polypeptide fragments, and polypeptides comprising any of these fragments are identified and characterized by any (one or more) of the five criteria described above.

Murine and exemplary humanized variable domain sequences of an anti-TES7 antibody are provided in FIGS. 11 and 12 (light chain and heavy chain, respectively). These sequences are provided by way of illustration not limitation, and different sequences as well as fragments and variants of the provided sequences, are encompassed within the scope of this invention. In some embodiments, chimeric anti-TES7 antibodies of this invention comprise the murine variable domain sequences of FIGS. 11 and 12.

In some embodiments, the antibodies, polypeptides and proteins of the invention that bind to TES7 are antibodies, polypeptides and proteins that competitively inhibit preferential binding of a herein-specified anti-TES7 antibody to TES7. In some embodiments, the antibodies, the polypeptides and the proteins preferentially bind to the same epitope on TES7 as the antibody mu-anti-TES7 preferentially binds.

Accordingly, the invention provides any of the following (or compositions, including pharmaceutical compositions, comprising any of the following): (a) an antibody produced by the host cell with a deposit number identified above or its progeny; (b) a humanized form of such an antibody; (c) an antibody comprising one or more of the light chain and/or heavy chain variable regions of such an antibody; (d) a chimeric antibody comprising variable regions homologous or derived from variable regions of a heavy chain and a light chain of such an antibody, and constant regions homologous or derived from constant regions of a heavy chain and a light chain of a human antibody; (e) an antibody comprising one or more of the light chain and/or heavy chain CDRs (at least one, two, three, four, five, or six) of such an antibody; (f) an antibody comprising a heavy and/or a light chain of such an antibody; (g) a human antibody that is equivalent to such an antibody. A humanized form of the antibody may or may not have CDRs identical to that original antibody, or antibody produced by a host cell with a deposit number identified above. Determination of CDR regions is well within the skill of the art. In some embodiments, the invention provides an antibody which comprises at least one CDR that is substantially homologous to at least one CDR, at least two, at least three, at least four, at least 5 CDRs of an antibody produced by one of the above-identified deposited hybridomas (or, in some embodiments substantially homologous to all 6 CDRs of one of these antibodies, or derived from one of these antibodies), or antibody produced by the host cell with a deposit number identified above. Other embodiments include antibodies that have at least two, three, four, five, or six CDR(s) that are substantially homologous to at least two, three, four, five or six CDRs of an antibody produced from a hybridoma deposited as identified herein, or derived from such an antibody. It is understood that, for purposes of this invention, binding specificity and/or overall activity (which may be in terms of delivering a chemotherapeutic agent to or into cancerous cells to reduce the growth and/or proliferation of cancer cells, to induce apoptotic cell death in the cancer cell, to delay the development of metastasis, and/or treating palliatively) is generally retained, although the extent of activity may vary compared to an antibody produced by a deposited hybridoma (may be greater or lesser). The invention also provides methods of making any of these antibodies. Methods of making antibodies are known in the art and are described herein.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

In some embodiments of this invention, cells of this invention that express TES7, a portion of TES7, anti-TES7 antibodies or other TES7-binding polypeptides of this invention are administered directly to an individual to modulate their in vivo TES7 biological activity.

VIII. Methods of Using TES7 Modulators and Anti-TES7 Antibodies for Therapeutic Purposes Monoclonal antibodies to TES7 may be used for therapeutic purposes in individuals with cancer or other diseases. Therapy with anti-TES7 antibodies can involve formation of complexes both in vitro and in vivo as described above. In one embodiment, monoclonal antibody anti-TES7 can bind to and reduce the proliferation of cancerous cells. It is understood that the antibody is administered at a concentration that promotes binding at physiological (e.g., in vivo) conditions. In another embodiment, monoclonal antibodies to TES7 can be used for immunotherapy directed at cancerous cells of different tissues such as colon, lung, breast, prostate, ovary, pancreas, kidney and other types of cancer such as sarcoma. In another embodiment, monoclonal antibody anti-TES7 alone can bind to and reduce cell division in the cancer cell. In another embodiment, monoclonal antibody anti-TES7 can bind to cancerous cells and delay the development of metastasis. In yet another embodiment, an individual with cancer is given palliative treatment with anti-TES7 antibody. Palliative treatment of a cancer individual involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

In such situations, the anti-TES7 antibody may be administered with agents that enhance or direct an individual's own immune response, such as an agent that strengthens ADCC.

In yet another embodiment, anti-TES7 antibody be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the antibody and thus eliminate cancerous or diseased cells. Without being limited to any particular theory, the anti-TES7 antibody is internalized by the cell bearing TES7 at its surface, thus delivering the conjugated moiety to the cell to induce the therapeutic effect. In yet another embodiment, the antibody can be employed as adjuvant therapy at the time of the surgical removal of a cancer expressing the antigen in order to delay the development of metastasis. The antibody can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

Cell cycle dosing is contemplated in the practice of this invention. In such embodiments, a chemotherapeutic agent is used to synchronize the cell cycle of the tumor or other target diseased cells at a pre-determined stage. Subsequently, administration of the anti-TES7 antibody of this invention (alone or with an additional therapeutic moiety) is made. In alternative embodiments, an anti-TES7 antibody is used to synchronize the cell cycle and reduce cell division prior to administration of a second round of treatment; the second round may be administration of an anti-TES7 antibody and/or an additional therapeutic moiety.

Chemotherapeutic agents include radioactive molecules, toxins, also referred to as cytotoxins or cytotoxic agents, which includes any agent that is detrimental to the viability of cancerous cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), antimitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin alfa, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon alfa-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In a preferred embodiment, the cytotoxin is especially effective in dividing or rapidly dividing cells, such that non-dividing cells are relatively spared from the toxic effects.

The antibodies of the invention can be internalized within the diseased or carcinoma cells to which they bind and are therefore particularly useful for therapeutic applications, for example, delivering into the cells toxins that need to be internalized for their adverse activity. Examples of such toxins include, but not limited to, saporin, calicheamicin, auristatin, and maytansinoid.

The antibodies or polypeptides of the invention can be associated (including conjugated or linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the chemotherapeutic molecule at any location along the antibody so long as the antibody is able to bind its target TES7.

A toxin or a chemotherapeutic agent may be administered concurrently with (before, after, or during administration), or coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and chemotherapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a chemotherapeutic agent via a microcarrier. Microcarrier refers to a biodegradable or a non-biodegradable particle which is insoluble in water and which has a size of less than about 150, 120 or 100 mm in size, more commonly less than about 50-60 μm, preferably less than about 10, 5, 2.5, 2 or 1.5 μm. Microcarriers include "nanocarriers", which are microcarriers have a size of less than about 1 μm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5] undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or chemotherapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen et al., *Biochem. Biophys. Res. Commun.* 102:1048-1054 (1981) for the preparation of conjugates of daunorubicin with macromolecular carriers; Yang et al., *J. Natl. Canc. Inst.* 80:1154-1159 (1988) for the preparation of conjugates of daunorubicin to an anti-melanoma antibody; Dillman et al., *Cancer Res.* 48:6097-6102 (1988) for using an acid-labile linker in a similar fashion to prepare conjugates of daunorubicin with an anti-T cell antibody; Trouet et al., *Proc. Natl. Acad. Sci.* 79:626-629 (1982) for linking daunorubicin to an antibody via a peptide spacer arm.

An antibody (or polypeptide) of this invention may be conjugated (linked) to a radioactive molecule by any method known to the art. For a discussion of methods for radiolabeling antibody see "Cancer Therapy with Monoclonal AntibodiesT", D. M. Goldenberg ed. (CRC Press, Boca Raton, 1995).

Alternatively, an antibody can be conjugated to a second antibody to form an antibody heteroconjugate as described by Segal in U.S. Pat. No. 4,676,980. The formation of cross-linked antibodies can target the immune system to specific types of cells, for example, cancer or diseased cells expressing TES7.

This invention also provides methods of delaying development of metastasis in an individual with cancer (including, but not limited to, prostate, lung, or kidney cancer) using an anti-TES7 antibody or other embodiments that bind to TES7 in combination with a chemotherapeutic agent, or linked to a chemotherapeutic agent. In some embodiments, the antibody is a humanized or chimeric form of a non-human anti-TES7 antibody.

In yet another embodiment, the antibody can be employed as adjuvant therapy at the time of the surgical removal of a cancer expressing the antigen in order to delay the development of metastasis. The antibody or antibody associated with a chemotherapeutic agent can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

In yet another embodiment, any of the TES7 binding embodiments described herein can bind to TES7-expressing cancerous cells and induces an active immune response against the cancerous cells expressing TES7. In some cases, the active immune response can cause the death of the cancerous cells (e.g., antibody binding to cancer cells inducing apoptotic cell death), or inhibit the growth (e.g., block cells cycle progression) of the cancerous cells. In other cases, any of the novel antibodies described herein can bind to cancerous cells and antibody dependent cellular cytotoxicity (ADCC) can eliminate cancerous cells to which anti-TES7 binds. Accordingly, the invention provides methods of stimulating an immune response comprising administering any of the compositions described herein.

In some cases, antibody binding can also activate both cellular and humoral immune responses and recruit more natural killer cells or increased production of cytokines (e.g., IL-2, IFN-gamma, IL-12, TNF-alpha, TNF-beta, etc.) that further activate an individual's immune system to destroy cancerous cells. In yet another embodiment, anti-TES7 antibodies can bind to cancerous cells, and macrophages or other phagocytic cell can opsonize the cancerous cells.

Various formulations of anti-TES7 antibodies or fragments thereof may be used for administration. In some embodiments, anti-TES7 antibodies or fragments thereof may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington, The Science and Practice of Pharmacy* 20th Ed. Mack Publishing (2000).

Suitable formulations for oral administration include hard or soft gelatin capsules, pills, tablets, including coated tablets, elixirs, suspensions, syrups or inhalations and controlled release forms thereof.

Generally, these agents are formulated for administration by injection (e.g., intraperitoneally, intravenously, subcutaneously, intramuscularly, etc.), although other forms of administration (e.g., oral, mucosal, etc) can be also used. Accordingly, anti-TES7 antibodies are preferably combined with pharmaceutically acceptable vehicles such as saline, Ringer's solution, dextrose solution, and the like.

The particular dosage regimen, i.e., dose, timing and repetition, will depend on the particular individual and that individual's medical history. Generally, a dose of at least about 100 ug/kg body weight, more preferably at least about 250 ug/kg body weight, even more preferably at least about 750 ug/kg body weight, even more preferably at least about 3 mg/kg body weight, even more preferably at least about 5 mg/kg body weight, even more preferably at least about 10 mg/kg body weight is administered.

Empirical considerations, such as the half-life, generally will contribute to the determination of the dosage. Antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of anti-TES7 antibodies may be appropriate. Various formulations and devices for achieving sustained release are known in the art.

In one embodiment, dosages for anti-TES7 antibodies may be determined empirically in individuals who have been given one or more administration(s). Individuals are given incremental dosages of an anti-TES7 antibody. To assess efficacy of anti-TES7 antibodies, a marker of the specific cancer disease state can be followed. These include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. Anti-TES7 antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. In one embodiment, a mixture of different anti-TES7 antibodies is used. A mixture of antibodies, as they are often denoted in the art, may be particularly useful in treating a broader range of population of individuals.

The following examples are provided to illustrate, but not to limit, the invention.

EXAMPLES

Example 1

Preparation of Human Fetal Testis Cells as an Immunogen

Human fetal testes of gestational age between 10 to 18 weeks were obtained from Advanced Biosciences Research at Alameda County, Calif. Testes were procured and shipped to the lab in tissue culture medium on wet ice. Immediately upon arrival, the testes were transferred to wash medium (F12/DME (1:1)). The testes were minced into 1 mm cubes with surgical scissors in a 100 mm dry culture dish. The tissue pieces were plated in 10 ml of a defined serum-free medium, herein referred to as testis medium.

The medium used for this example contained the following components at the indicated final concentrations: F12/DME (1:1), Insulin, 10 µg/ml, Transferrin, 100 mg/ml, EGF, 50 µg/ml, Ethanolamine, $10^{-3}$ M, Phosphoethanolamine, $10^{-3}$ M, Triiodothyronine (T3), $10^{-9}$ M, Selenium, $2.5 \times 10^{-5}$ M, Vitamin E, 5 µg/ml, and Gentamycin, 100 µg/ml. While a variety of commonly used cell culture media may be used in the practice of this invention, presently preferred embodiments use serum-free based cell culture media.

The tissue pieces were transferred into a 15 ml centrifuge tube and the tissue pieces were centrifuged at 1000×g for 5 minutes. The tissue pieces were resuspended in testis medium, penicillin/streptomycin (1×) and collagenase/dispase (0.1%) and incubated at 4° C. overnight. The following day, centrifuge the digested tissue pieces were centrifuged at 1000×g for 5 minutes and washed twice with testis medium. The pellet was resuspended in 10 ml testis medium and cultured in fibronectin-precoated 10 cm plates.

To harvest the cells, the cell monolayers were rinsed once with calcium- and magnesium-free Hanks saline solution, incubated with Accutase (eBioscience) in Hanks saline solution at 37° C. for 15 minutes. The cells were detached from the culture surface by gentle pipetting. The cell suspension was pelleted by centrifugation at 1000×g for 5 minutes. The supernatant was removed and cells were resuspended in serum-free medium with non-denaturing adjuvant as appropriate.

Example 2

Generation of Monoclonal Antibodies

A non-denaturing adjuvant (Ribi, R730, Corixa, Hamilton Mont.) was rehydrated to 2 ml in phosphate buffered saline. 100 µl of this rehydrated adjuvant was then gently mixed with some of the cell pellet from Example 1 to be used for immunization. Approximately $10^6$ human fetal testis cells per mouse were injected into Balb/c mice via footpad, approximately once or twice a week. The precise immunization schedule is as follows: Day zero, immunization plus Ribi. Day 3, immunization plus Ribi. Day 7, immunization plus Ribi. Day 24, immunization minus Ribi. Day 29, immunization minus Ribi. Day 32, immunization minus Ribi. Day 36, immunization minus Ribi. Day 44, immunization minus Ribi. Day 51, immunization minus Ribi. Day 69, bleed for titer test. Day 71, immunization plus Ribi. Day 74, immunization plus Ribi. Day 81, immunization plus Ribi. Day 91, prefusion boost (no Ribi). Day 104, harvest nodes for fusion.

At Day 69, a drop of blood was drawn from the tail of each immunized animal to test the titer of antibodies against human fetal kidney cells using FACS analysis. When the titer reached at least 1:2000, the mice were sacrificed using $CO_2$ followed by cervical dislocation. Lymph nodes were harvested for hybridoma preparation.

Lymphocytes from mice were fused with the mouse myeloma line X63-Ag8.653 using 35% polyethylene glycol 4000. On day 10 following the fusion, the hybridoma supernatants were screened for the presence of human fetal kidney cells-specific monoclonal antibodies by fluorescence activated cell sorting (FACS). Conditioned medium from each hybridoma was incubated for 30 minutes with an aliquot of human fetal kidney cells. After incubation, the cell samples were washed, resuspended in 0.1 ml diluent and incubated with 1 µg/ml of FITC conjugated F(ab')2 fragment of goat anti-mouse IgG for 30 min at 4° C. The cells were washed, resuspended in 0.2 ml FACS diluent and analyzed using a FACScan cell analyzer (Becton Dickinson; San Jose, Calif.). Hybridoma clones were selected for further expansion, cloning, and characterization based on their binding to the surface of the human fetal kidney cells by FACS. A hybridoma making a monoclonal antibody designated mu-anti-TES7 that binds an antigen designated Ag-TES7 and an epitope on that antigen was selected.

Example 3

Purification of Anti-TES7 Antibodies, Including mu-anti-TES7

Human fetal testis cells such as but not limited to SKMES-1, 786-O, and Colo205 cell lines were detached from tissue culture flasks in the presence of 10.0 mM EDTA, centrifuged at 1400 rpm for 5 minutes and resuspended in PBS containing 1% BSA and 2 mM EDTA (FACS diluent). The cells were counted and adjusted to $10^7$ cells/ml. About 0.1 ml of cells were incubated with 100 µl FACS diluent for 30 minutes at 37° C. Monoclonal antibodies that bind to the human fetal testis cells were purified from tissue culture supernatant using protein-G affinity chromatography. The following materials were used for the antibody purification process: hybridoma tissue culture supernatant, Immunopure (G) IgG binding buffer (Pierce #21011 Rockford, Ill.), Immunopure IgG Elution Buffer (Pierce #21009), concentrated HCl (for adjusting pH), Corning 1 liter PES (polyether sulfone), 0.22 µm filter (Corning #431098, Corning, N.Y.), Amersham Pharmacia AKTA Explorer System (Amersham Biosciences, Piscataway, N.J.), Protein-G Sepharose 4 Fast Flow (Amersham Biosciences #17-0618-03), Stripping buffer consisting of 3M Potassium thiocyanate/50 mM Tris pH 7.8, and PBS (phosphate buffered saline), 3M Tris pH 9.0.

To purify the mouse anti-huTES7 antibody referred to herein as mu-anti-TES7, the volume of the supernatant was measured and an equal volume of binding buffer was added to the supernatant. The mixture was allowed to equilibrate to room temperature. The supernatant was clarified by passage through a 0.22 μm filter. The supernatant was loaded onto a protein-G Sepharose column using the AKTA Explorer system (Amersham Biosciences) and then washed with 5-10 column volumes of binding buffer. The monoclonal antibody was eluted with the elution buffer, and fractions were collected. The fractions were neutralized upon elution with the addition of 3M Tris, pH 9.0 to empty tubes (¹⁄₆₀ volume of the fractions). The peak fractions containing the monoclonal antibody were pooled. The pooled samples was injected into a pre-wetted slidealyzer cassette (10,000 MW cutoff; Pierce #66810) and dialyzed in 1×PBS at 4° C. (with 3 buffer changes of at least 4 hours of dialysis per change). The purified monoclonal antibody was sterile filtered (0.2 μm Acrodisc) and stored at 2-8° C.

A sample of purified antibody is taken for determination of concentration by UV absorbance ($A_{280}$) and SDS-polyacrylimide gel electrophoresis (SDS-PAGE). SDS-PAGE is run under both non-reducing and reducing conditions for analysis of molecular weight, identification of the typical banding pattern of monoclonal antibodies and assessment of purity.

After purification of the mu-anti-TES7 monoclonal antibody from the hybridoma supernatant, it was re-tested for binding to human fetal testis cells. The cell samples were prepared as described above and incubated with the purified antibody at various concentrations. After incubation the cells were washed, resuspended in 0.1 ml diluent and incubated with 1 μg of FITC conjugated F(ab)'2 fragment of goat anti-mouse IgG for 30 minutes at 4° C. The cells were washed, resuspended in 0.5 ml FACS diluent and analyzed using a FACScan cell sorter (Becton Dickinson, San Jose, Calif.). A shift to the right on the FACScan histogram indicated that the purified antibody still bound to human fetal testis cells.

Example 4

Biochemical Analysis of TES7 Expression in Cancer Cell Line SW948 and with Recombinant 4-Ig B7H3

Colorectal adenocarcinoma SW948 (ATCC# CCL-237) cells were grown to confluency on 175 cm² culture dishes. The confluent monolayer was washed three times with Hank's Balanced Salt Solution (HBSS+ containing no sodium bicarbonate or phenol red; buffered with 10 mM HEPES, pH 7.4; Sigma Chemicals) and biotinylated with 200 μg of sulfo-NHS-LC-biotin (Pierce Endogen) for 30 minutes at room temperature. The cells were then washed with HBSS+ containing 0.1M Tris, pH 7.4 (Sigma Chemicals) and incubated in HBSS+ containing 0.1M Tris, pH 7.4 for 15 minutes at room temperature. The cells were finally washed three times with HBSS+ and lysed by incubation for 5 minutes, on ice, in lysis buffer (HBSS+ with 2% Triton X-100, 2 mM PMSF, 0.1% sodium azide, and 1 tablet per 5 ml lysis buffer of EDTA free complete mini-protease cocktail (Roche Molecular Biochemicals)).

Cells were scraped in lysis buffer and lysates collected. Lysates were centrifuged at 14,000-×g for one hour at 4° C. The clarified lysate was then pre-cleared for 2 hours at 4° C. with 5 μl of human IgG conjugated (1 mg/ml) CNBr 4 MB sepharose beads (Amersham Pharmacia). Human IgG beads were centrifuged and removed, and then the pre-cleared lysate was then incubated with monoclonal antibody mu-anti-TES7 conjugated to CNBr 4 MB sepharose beads (conjugated at 1 mg/ml) for 2 hours at 4° C. The mu-anti-TES7 beads were centrifuged and removed after the 2-hour incubation. Both the human IgG and the mu-anti-TES7 beads were individually washed three times with 1 ml of lysis buffer and then washed three times with 1 ml HBSS+. The washed beads were eluted by the addition of 30 μl of SDS-PAGE sample buffer and boiling at 99° C. for 5 minutes.

The samples were then resolved on a 4-20% Novex gradient gel (Invitrogen), and transferred onto 0.2 μm nitrocellulose membrane (Invitrogen) and visualized by horseradish peroxidase (HRP) conjugated streptavidin (Pierce Endogen). For detection with HRP conjugated streptavidin, the nitrocellulose was first blocked for 1 hour with blocking buffer (5% non-fat dry milk in Tris-buffered saline with 0.05% Tween-20 (TBST)). HRP conjugated streptavidin was diluted into TBST at 1 μg/ml and exposed to the nitrocellulose for 30 minutes at room temperature. The nitrocellulose was washed three times in TBST before visualization with ECL+ (Amersham). Results showed a specific band using mu-anti-TES7 beads of approximately 110 kDa in size (results not shown).

To confirm the antigen target of mu-anti-TES7 was B7H3, 100 ng of recombinant 4Ig-B7H3 protein (HIS-Tagged and carrier-free, R&D Systems) was separated by electrophoresis on a 4-20% gradient SDS gel under reducing and non-reducing conditions utilizing standard protocols, similar to those described above. The proteins were transferred to 0.2 μm nitrocellulose membrane (Invitrogen), and blocked in 5% non-fat dry milk in HBSS for 2 hours at room temperature or at 4° C. overnight. Primary antibody (mu-anti-TES7) at a concentration of 5 μg/ml in blocking buffer (5% non-fat dry milk in HBSS with 0.1% Tween 20) was added for at least one hour at room temperature. The membrane was washed three times for 10 minutes each in HBSS, 0.1% Tween 20 and secondary antibody (donkey anti-mouse, H+L, HRP-conjugated, Jackson Laboratories) was added for an hour at room temperature. The blot was washed three time with HBSS, 0.1% Tween 20 before visualization with ECL+(Amersham).

Figure 3:
FIG. 3 shows results of a Western blot experiment using recombinant human B7H3 and mu-anti-TES7 antibodies.

Results showed mu-anti-TES7 recognizes human recombinant 4Ig B7H3 only under non-reducing conditions in western blot analysis, as shown in FIG. 3. The size difference between the recombinant 4Ig B7H3 (80-85 kDa) and the B7H3 pulled down using mu-anti-TES7 beads from biotinylated cell lysates (approximately 100 to 110 kDa) is probably due to the recombinant 4IgG B7H3 protein starts at Gly 27 and the B7H3 protein from biotinylated cell lysates is the full-length molecule.

Example 5

Immunohistochemistry Methods

Anti-TES7 antibodies such as mu-anti-TES7 were screened on frozen normal human and tumor tissue samples from surgical biopsies and/or autopsy specimen. The frozen tissue samples were embedded in OCT compound and quick-frozen in isopentane with dry ice. Cryosections were cut with a Leica 3050 CM mictrotome at thickness of 8-10 μm and thaw-mounted on SuperFrost Plus slides (VWR #48311-703) and were allowed to air-dry for 2 hours at room temperature. The sections were fixed with 75% acetone/25% ethanol for 10 minutes at room temperature and allowed to air-dry 1-2 hours at room temperature. The fixed sections were stored at −80° C. until use.

For immunohistochemistry, the tissue sections were retrieved, allowed to slowly equilibrate to room temperature from −80° C., washed in Tris buffered 0.05% Tween (TB-T) three times for 5 minutes each time, and blocked in blocking buffer (TB-T, 5% normal goat serum and 100 μg/ml avidin) for 20 minutes at room temperature. The slides were then incubated with the mu-anti-TES7 and control monoclonal antibodies diluted in blocking buffer (1-5 μg/ml) for 60-90 minutes at room temperature or overnight at 4° C. The sections were then washed three times with the blocking buffer and then blocked with a hydrogen peroxidase (1-3%) biotin (d-biotin, 30 µg/ml) block in TB-T was done for 20 minutes at room temperature. A third wash with TB-T was then performed three times as described above. The Sections were incubated in blocking buffer with a secondary biotinylated goat anti-mouse IgG+IgM (H+L) antibody at room temperature for 30 minutes. Another wash was performed with TB-T three times at 5 minutes each. Avidin biotin peroxidase complex formation was then accomplished by adding the premade ABC solution (Vectastain ABC Elite Kit) according to manufacturer's directions and the slides were incubated for 30 minutes at room temperature. Slides were then washed 2 times with TB-T and then once with deionized water for 5 minutes each. A DAB substrate (10 ml 10×DAB solution, 90 ml Tris buffer, pH 7.6, and 100 µl 3% H2O2) was added to the slides for 30 minutes at room temperature to allow for the formation of colored precipitate and visualization of the bound primary antibody. The slides were then counterstained with hematoxylin.

The binding of mu-anti-TES7 antibody to a variety of normal human and tumor tissues was assessed. The results were scored as "+/−" for equivocal staining, "1+" for weak positive staining, "2+" for moderate positive staining, "3+" for strong positive staining. Focal staining is indicated.

An alternative IHC protocol (HRP polymer conjugated goat-anti-mouse IgG) using frozen normal and tumor tissue was also performed using mu-anti-TES7 antibody. The cancer tissues assayed included prostate, lung, colon and breast cancers. Four cases from each tumor type were evaluated, except prostate where three cases were evaluated, using this alternative IHC protocol. The normal tissue panel included heart, lung, liver, kidney, pancreas, colon and skin (one specimen from each tissue type). The assay was qualified using H&E staining to ensure correct diagnosis and good morphology. Positive control fetal prostate tissue was also used and a corresponding mouse IgG antibody was used as an isotype control. Mu-anti-TES7 IHC was run using an antibody concentration of 1 µg/ml incubated for 60 minutes at room temperature on acetone-fixed frozen human specimens. HRP polymer conjugated goat anti-mouse IgG (DAKO) was used as a linked secondary antibody. DAB was the chromogen used to visualize the antibody binding.

For convenience, a summary of the combined results of several experiments using frozen surgical normal tissue from different sources is shown below in Table 1 (traditional ABC protocol). Table 2 shows the binding of mu-anti-TES7 to normal tissues using HRP polymer conjugated IHC methods. Table 3 shows the binding of mu-anti-TES7 antibody to tumor tissue samples using traditional ABC protocol. Table 4 shows mu-anti-TES7 antibody binding to tumor tissue samples using HRP polymer conjugated IHC methods. Table 5 summarizes the binding of mu-anti-TES7 antibodies to an expanded panel of prostate and pancreatic tissues. Table 6 summarizes the binding of mu-anti-TES7 antibody to human fetal tissues of 10-12 weeks and 18-22 weeks. Briefly, many fetal tissues were positive for TES7 staining, particularly in the areas of new organ formation and new bone formation.

TABLE 1

Distribution of TES7 in normal human tissues using standard HRP conjugated secondary and ABC amplification protocols

| Tissue Type | Results |
| --- | --- |
| Skin | +/− staining on basal epidermis |
| Lung | Negative |
| Kidney | Negative |
| Liver | Negative |
| Pancreas | Negative |
| Kidney, fetal | 2+ staining in tubules, focal |
| Prostate, fetal | 2+ staining, focal |
| Uterus | Some focal 1+ smooth muscle |

TABLE 2

Distribution of TES7 in normal human tissues using HRP polymer conjugated IHC methods

| Tissue Type | Results |
| --- | --- |
| Pancreas | Negative |
| Lung | Negative |
| Liver | Negative |
| Kidney | 2+ cytoplasmic staining on kidney mesothelium |
| Colon | 1+ (25%) membrane staining |
| Heart | Negative |
| Skin | Negative |

TABLE 3

Distribution of TES7 in human tumor tissues using standard ABC protocol

| Tissue Type | Results |
| --- | --- |
| Lung | Negative |
| Kidney | +/− |
| Colon | Negative |
| Prostate | +/++ |
| Breast | Negative |
| Ovary | Negative |
| Pancreas | Negative |

TABLE 4

Distribution of TES7 on human tumor tissues using HRP polymer conjugated IHC method

| Tumor Type | Results |
| --- | --- |
| Lung (squamous carcinoma) | 1-3+ staining on 20% of tumor (cytoplasmic and membrane); 3+ staining on fibroblasts and stroma; 2+ staining on inflammatory cells |
| Lung (squamous carcinoma) | 3+ staining on 90% of tumor (cytoplasmic and membrane); 1-2+ staining on endothelium; 3+ staining on fibroblasts; 1+ staining on stroma; 2+ staining on inflammatory cells; 1+ staining on nerve |
| Lung (adenocarcinoma) | 3+ staining on 10% of tumor (cytoplasmic); 2+ staining on endothelium; 1+ staining on fibroblasts; 2+ staining on inflammatory cells |

TABLE 4-continued

Distribution of TES7 on human tumor tissues using HRP polymer conjugated IHC method

| Tumor Type | Results |
| --- | --- |
| Lung (large cell carcinoma) | 2+ staining on 5% of tumor (cytoplasmic and membrane); 1+ staining on endothelium; 3+ staining on fibroblasts and stroma and 1+ staining on inflammatory cells |
| Breast (adenocarcinoma) | 3+ staining on 70% of tumor (cytoplasmic and membrane); 2+ on endothelium; 2+ staining on smooth muscle; 3+ on fibroblasts; 1+ on inflammatory cells |
| Breast (infiltrating ductal carcinoma) | 3+ staining on 80% of tumor (cytoplasmic and membrane); 1+ staining on smooth muscle; 3+ staining on fibroblasts; 1+ staining on inflammatory cells. |
| Breast (infiltrating ductal carcinoma) | 3+ staining on 100% of tumor (cytoplasmic and membrane); 1+ staining on endothelium, stroma, nerve and inflammatory cells; 3+ staining on fibroblasts |
| Breast (infiltrating ductal carcinoma) | 3+ staining on 80% of tumor (cytoplasmic and membrane); 2+ staining on fibroblasts; 1+ staining on stroma and inflammatory cells |
| Colon adenocarcinoma | Negative |
| Colon adenocarcinoma | 1-3+ staining on 50% of tumor (cytoplasmic); 3+ staining on endothelium, fibroblasts and inflammatory cells; 2+ staining on stroma |
| Colon adenocarcinoma | 1-3+ staining on 60% of tumor (cytoplasmic and membrane); 3+ staining on endothelium and fibroblasts; 2+ staining on stroma and inflammatory cells |
| Colon adenocarcinoma | 1+ staining on 20% of tumor (cytoplasmic); 3+ staining on fibroblasts, stoma, and inflammatory cells; 1+ staining on endothelium |
| Prostate carcinoma | 3+ staining on 60% of tumor (cytoplasmic and membrane); 2+ staining on fibroblasts; 1+ staining on endothelium, stroma and inflammatory cells |
| Prostate carcinoma | 2-3+ staining on 80% of tumor (cytoplasmic and membrane) |
| Prostate carcinoma | 1-3+ staining on 80% of tumor (cytoplasmic and membrane); 1+ staining on endothelium and inflammatory cells |

TABLE 5

Distribution of TES7 in expanded panel of prostatic and pancreatic tissues

| Tissue Type | Results |
| --- | --- |
| Prostate Adenocarcinoma | 23/27 tissue samples were positive (85%) |
| Benign Prostatic Hypertrophy | 8/12 tissue samples were positive (67%) |
| Pancreatic Carcinoma: Epithelium | 6/13 tissue samples were positive (46%) |
| Pancreatic Carcinoma: Stroma & blood vessels | 11/13 tissue samples were positive (85%) |
| Normal Pancreas: Acini/islets | 1/4 tissue samples were positive (25%) |
| Normal Pancreas: Fibrosis/interstitial tissue | 1/4 tissue samples were positive (25%) |

TABLE 6

Distribution of TES7 in Human Fetal Tissues

| Tissue Type | Fetal Tissue 10-12 weeks TES7 IHC Results | Fetal Tissue 18-22 weeks TES7 IHC Results |
| --- | --- | --- |
| Adrenal | 1-2+ uniform staining on all layers | Not Done |
| Aorta & Great Vessels | Smooth muscle: 1+ uniform cytoplasmic staining | Not Done |
| Bladder | Transitional epithelium: 2+ uniform cytoplasmic staining | Not Done |
| Skin | Epidermis: basal layer: 2+ uniform cytoplasmic staining; Capillaries & Mesenchyme: 1-2+ uniform cytoplasmic staining | Hair follicle/Outer layer: +/− to 1+ staining |
| Small Intestine | Mucosa: 1-2+ cytoplasm and apical membrane (mostly in crypt) staining on 10-50% of cells | Not Done |
| Testis | Leydig cells: Uniform 1+ staining | Leydig cells: Uniform 1+ staining |
| Pelvic Bones | Bone/Mesenchyme Junction: 1-2+ uniform cytoplasmic staining | Not Done |

TABLE 6-continued

Distribution of TES7 in Human Fetal Tissues

| Tissue Type | Fetal Tissue 10-12 weeks TES7 IHC Results | Fetal Tissue 18-22 weeks TES7 IHC Results |
|---|---|---|
| Prostate | Epithelium: 1-2+ uniform cytoplasmic staining; Mesenchyme: +/– to 1+ staining | Epithelium: 2-3+ uniform cytoplasmic and apical membrane staining; Stroma: 1-2+ uniform cytoplasmic staining |
| Ribcage | Rib/Mesenchyme Junction: 2-3+ cytoplasmic staining; Mesenchyme surrounding ribs: 2+ cytoplasmic staining | Not Done |
| Lung | Forming air spaces: 1-2+ uniform cytoplasmic and apical membrane staining on 50-75% of cells; Surrounding mesenchyme: +/– to 1+ diffused staining | Forming air spaces: 2-3+ uniform staining; Mesenchyme: +/– to 1+ cytoplasmic staining |
| Ovary | Not Done | 1+ staining on ovum and stroma |
| Pancreas | Main duct epithelium: +/– to 1+ uniform cytoplasmic staining | Forming beta islet cells: 1-2+ cytoplasmic staining; Blood vessels/ducts: focal 1-2+ cytoplasmic staining |
| Heart | Cardiac muscle: 1-2+ uniform cytoplasmic staining | Not Done |
| Kidney | Nephrons: 2-3+ cytoplasmic and apical membrane staining (50-75% cells) Blastema: 1+ staining on cytoplasmic granules and cell membrane | Not Done |
| Liver | Hepatocytes: Negative Blood cell blasts: 1-2+ staining on 10-50% of cells | Smooth muscle of duct: 1-2+ cytoplasmic staining; Blood cell blasts: +/– cytoplasmic staining |
| Brain | Negative | Negative |
| Colon | Colonic Mucosa: 1-2+ cytoplasmic and apical membrane staining; Bowel Wall/Smooth Muscle/Fibroblasts: 1-2+ cytoplasmic staining | Colonic Mucosa: 1-2+ cytoplasmic staining on 50-75% of cells; Bowel wall/Smooth muscle/Fibroblasts: 1-2+ cytoplasmic staining; Blood vessels: 1-2+ staining; Anal Canal Mucosa/Basal layer: 1-3+ cytoplasmic staining |
| Esophagus | 1+ uniformed cytoplasmic staining | Not Done |

Example 6

Immunocytochemistry Results

Monoclonal antibody mu-anti-TES7 was used to test reactivity with various cell lines from different types of tissues. Identical immunohistochemistry protocols as described above were used for staining the CellArray. The results were scored as '+' for weak positive staining, '++' for moderate positive staining, '+++' for strong positive staining and '–' for negative staining.

Immunohistochemistry results were obtained using CellArray™ technology, as described in WO 01/43869. Cells from different established cell lines were removed from the growth surface without using proteases, packed and embedded in OCT compound. The cells were frozen and sectioned, then stained using a standard IHC protocol.

Results of the binding of the mu-anti-TES7 antibody to various established human normal and tumor cell lines are compiled for convenience in Table 7.

TABLE 7

Immunocytochemistry results-TES7

| Cell line | ATCC# | Organ | Cell Type | Reactivity, Cell Array |
|---|---|---|---|---|
| HMEC | CC-2251 (BioWhittaker) | Breast | Normal mammary epithelial | – |
| HuVEC | Primary | Endothelial cells | Normal human adult | +/– |
| BT474 | HTB-20 | Breast | Ductal carcinoma | + |
| MCF7 | HTB-22 | Breast | Adenocarcinoma | +/– |

TABLE 7-continued

Immunocytochemistry results-TES7

| Cell line | ATCC# | Organ | Cell Type | Reactivity, Cell Array |
|---|---|---|---|---|
| MDA175 | HB-25 | Breast | Ductal carcinoma | − |
| MDA361 | HB-27 | Breast | Adenocarcinoma | − |
| SK-BR-3 | HTB-30 | Breast | Adenocarcinoma | − |
| 9979 | RAVEN | Lung | Lung cancer line | − |
| A549 | CCL-185 | Lung | Carcinoma | − |
| CA130 | RAVEN | Lung | Small cell carcinoma | − |
| CaLu3 | HTB-55 | Lung | Adenocarcinoma | n/a |
| SKMES1 | HTB-58 | Lung | Squamous carcinoma | + |
| ES-2 | CRL-1978 | Ovary | Carcinoma | − |
| SKOV3 | HTB-77 | Ovary | Adenocarcinoma | − |
| 9926 | RAVEN | Pancreas | Adenocarcinoma | + |
| AsPC-1 | CRL-1682 | Pancreas | Adenocarcinoma | − |
| HPAFII | CRL-1997 | Pancreas | Adenocarcinoma | − |
| Hs700T | HTB-147 | Pancreas | Adenocarcinoma | +++ |
| Colo205 | CCL-222 | Colon | Ascites colorectal adenocarcinoma | − |
| HT-29 | HTB-38 | Colon | Colorectal adenocarcinoma | − |
| SW480 | CCL-228 | Colon | Colorectal adenocarcinoma | − |
| SW948 | CCL-237 | Colon | Colorectal adenocarcinoma | − |
| 293 | CRL-1573 | Kidney | Transformed with adenovirus5 DNA | +/− |
| 786-O | CRL-1932 | Kidney | Renal Cell Carcinoma | − |
| A498 | HTB-44 | Kidney | Carcinoma | +/− |
| Caki2 | HTB-47 | Kidney | Clear cell carcinoma | + |
| Cos 7 | CRL-1651 | Kidney (African Green Monkey) | SV40 transformed | − |
| RL65 | CRL-10345 | Lung (Rat) | | − |
| SVT2 | CCL-163.1 | Embryo (Mouse) | Fibroblast; SV40 transformed | − |
| 22RV1 | CRL-2505 | Prostate | Carcinoma | − |
| DU145 | HTB-81 | Prostate | Adenocarcinoma | − |
| LNCaP | CRL-1740 | Prostate | Carcinoma | − |
| PC3 | CRL-1435 | Prostate | Adenocarcinoma | − |
| TDH-1 | RAVEN | Prostate | Prostate cancer line | − |
| Hs746T | HTB-135 | Stomach | Carcinoma | − |
| NCI-N87 | CRL-5822 | Stomach | Carcinoma | − |

Example 7

Mu-anti-TES7 Binds to Cancer Stem Cells from Different Tumor Origins

Because of the expression of TES7 on fetal tissue, experiments to characterize TES7 expression on human cancer stem cells (as a cancer stem cell marker) were performed using mu-anti-TES7 antibody and a variety of human cancer stem cells from different tumor tissue origins. The analysis for TES7 on these human cancer stem cells was performed using standard FACS analysis methods that are commonly known and practiced in the art. Briefly, the human cancer stem cells were lifted from the flask using 2 ml of 0.2% collagenase/dispase for 5 minutes or until cells dissociated or released from the flask. The cells were triturated using a 5 ml pipette to eliminate any cell clumps and then transferred to a 15 ml conical tube and spun down for 5 minutes at 1200 rpm. The supernatant was removed and the cells were resuspended in 1 ml/T75 flask or 5 ml/T175 flask of Analysis Buffer (Hank's Balanced Salt Solution with 1% BSA). Cells were counted using a hemacytometer. 50,000 cells were mixed with mu-anti-TES7 monoclonal antibody at a concentration of 1 μg/ml in 50 μl volume. A goat anti-mouse IgG (H+L)-AlexaFluor 532 secondary antibody (Molecular Probes) was used at a concentration of 2 μg/ml. The cells were analyzed using a FACSCalibur or Guava machine. The results of TES7 expression on human cancer stem cells from a variety of tumor tissue sources are summarized in Table 8 below. "high" denotes a one log or greater shift in fluorescence intensity, "med" denotes a 0.5 to 1 log shift in fluorescence intensity, "low" denotes up to 0.5 log shift in fluorescence intensity and "−" denotes no shift in fluorescence intensity.

TABLE 8 mu-anti-TES7 binding to human cancer stem cells

| Human cancer stem cell | Fluorescence intensity |
|---|---|
| Breast | high |
| Colorectal | high |
| Lung | high |
| Merkel Cell Carcinoma | Med to high |
| Mantle Cell Lymphoma | high |
| Rectal carcinoma | Med to high |
| Pancreatic carcinoma | high |
| Prostate carcinoma | Med to high |
| Basal cell carcinoma | high |

As shown in Table 8, mu-anti-TES7 bound to all human cancer stem cells examined. mu-anti-TES7 binding caused a greater than one log shift (high) on breast, colorectal, lung, mantle cell lymphoma, pancreatic, and basal cell carcinoma stem cells. A 0.5 log to over a 1 log shift was seen on merkel cell carcinoma, rectal carcinoma and prostate carcinoma stem cells. This data suggests that 4Ig-B7H3 is expressed at a level and density on cancer stem cells sufficient for it to be useful as a potential marker for the identification of human cancer stem cells using anti-TES7 antibodies.

Example 8

Live-Cell ELISA Assay Using mu-anti-TES7 Antibody

The binding of the mu-anti-TES7 antibody to TES7 was tested using live cell ELISA. The following method was used, although other methods commonly known in the field are applicable. Cells (such as A375, HT-29, SKOV3, SKMES-1, SW480, SKBR-3, and HPAFII) were grown in 10% fetal bovine serum (FBS) containing media to confluency on tissue culture treated 96-well plates (Falcon). Cells were washed with PBS and then incubated with 50 µl of desired antibodies at a desired concentration in Hank's Balanced Salt Solution (HBSS) containing 1% BSA and 0.1% sodium azide for 1 hour at room temperature. The cells were then washed three times with 100 µl per well of HBSS before incubating with horseradish peroxidase (HRP) secondary antibody (50 µl per well diluted in HBSS) for 30 minutes at room temperature. The cells were finally washed three times with HBSS and the color change substrate (TMB substrate, KPL) was added to each well at 100 µl per well. The color change reaction was stopped with the addition of 100 µl per well of 1M phosphoric acid. The plates were then read at O.D. 450 nm. TES7 was positive in the live cell ELISA on A375 cells, displaying typical binding patterns that appear to correlate with the B7-H3 4Ig isoform.

Example 9

Mu-anti-TES7 Only Binds to the 4Ig Form of B7H3

Figure 4:
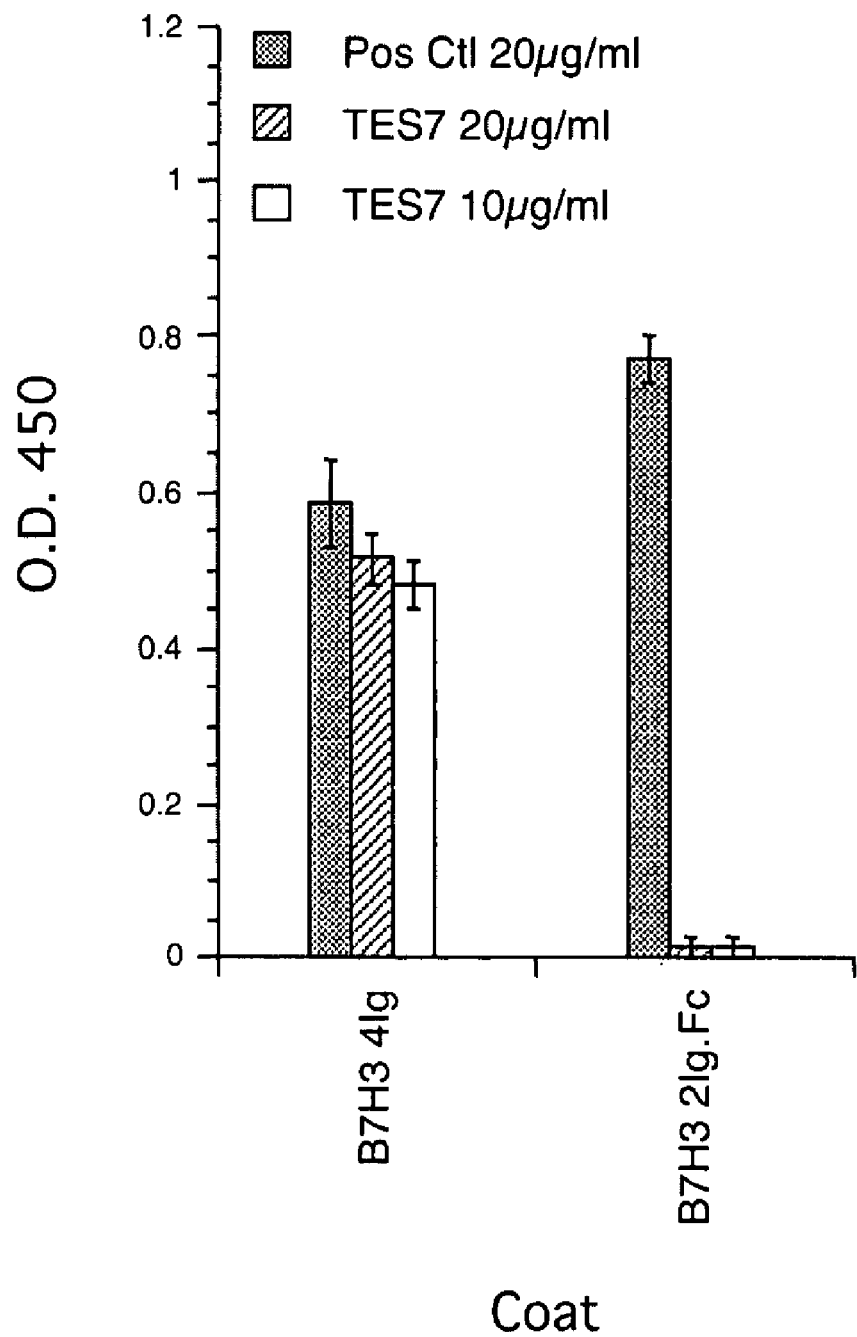
FIG. 4 shows the graphed results of an ELISA assay demonstrating a mu-anti-TES7 antibody preferentially binding to the four-Ig-loop B7-H3.

In order to determine the binding characteristics of mu-anti-TES7, ELISA experiments were performed using both the 2 Ig form of B7H3 and the 4 Ig form of B7H3. Recombinant human B7H3 proteins of both forms were purchased from R&D System (carrier-free). Both forms of B7H3 proteins were coated onto a 96-well plate at 2 µg/ml, 50 µl/well in HBSS+ (Hank's Balanced Salt Solution without phenol red). The plates were incubated at room temperature for 2 hours and then washed with HBSS+. The plates were then blocked with 150 µl blocking buffer (HBSS+ with 1.0% (w/v) BSA) for 30 minutes at room temperature. The blocking buffer was then removed and mu-anti-TES7 (10-20 µg/ml, 50 µl/well in blocking buffer) was added and allowed to incubate at room temperature for 1 hour. The plates were then washed with 150 µl blocking buffer three times. Secondary antibody (donkey anti-mouse IgG H+L HRP (Jackson Laboratories) diluted at a 1:1000 concentration in blocking buffer was added and incubated at room temperature for 30 minutes. The plates were then washed three times with 150 µl blocking buffer and developed with TMB substrate (KPL). The reaction was stopped with 1M phosphoric acid and the plates were read on a plate reader at O.D. 450 nm. As shown in FIG. 4, mu-anti-TES7 (at both the 10 µg/ml and 20-microgram/ml concentration) only bound to the 4Ig form of B7H3. The positive control (anti-B7H3 antibody) bound to both the 2Ig and the 4Ig form of B7H3.

Example 10

Comparison of mu-anti-TES7 to Other B7H3 Antibodies

In order to further investigate the binding profile of mu-anti-TES7, biochemical analysis was performed comparing mu-anti-TES7 antibody to other B7H3 antibodies. B7H3 antibodies have been described in the art, for example in WO 04/001381, hereby incorporated by reference. That application discloses the antibodies BLA8 and PA20. BLA8 is a monoclonal antibody to B7H3 that will recognize both the 4Ig and the 2Ig forms. PA20 is a monoclonal antibody to B7H3 that will only recognize the 4Ig form. PA20 was deposited with the ATCC on 23 Apr. 2002 with accession number PTA-4244 (hybridoma name Panc.1.5C10.5D11). STO5 is another anti-B7H3 antibody that only recognizes the 4Ig form of B7H3; STO5 was deposited with the ATCC as PTA-8576 on 8 Aug. 2007 (hybridoma name Stomach3.1E10.1G8).

Figure 5:
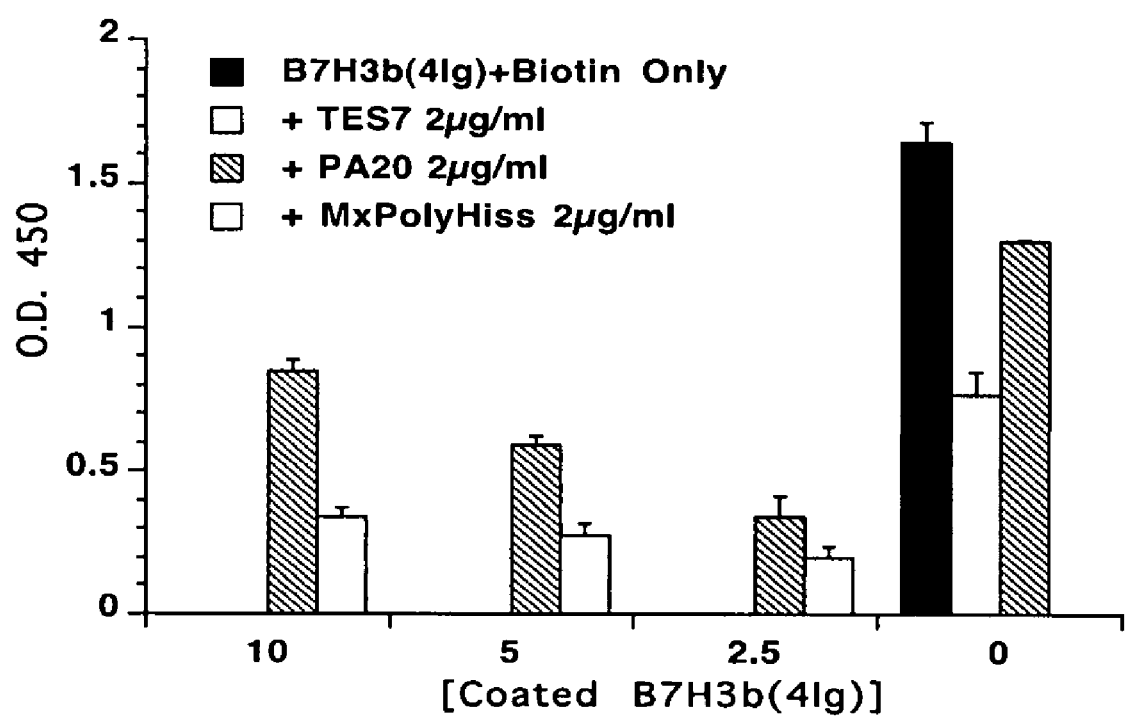
FIG. 5 shows that mu-anti-TES7 antibody reduced VEGF secretion in CSC-BMC co-culture.

To investigate whether mu-anti-TES7 can cross-link two molecules of 4Ig-B7H3, and ELISA was performed using 2.5, 5 or 10 µg/ml recombinant 4Ig-B7H3(His-tagged) coated down on a 96-well plate and either mu-anti-TES7 or PA20 antibody. In the "0" coat condition, as shown in FIG. 5, the wells were coated with biotinylated B7H3 (4Ig) and detected with mu-anti-TES7 or PA20 (both detected with HRP-conjugated donkey anti-mouse IgG) or streptavidin HRP in the biotinylated B7H3 only condition. A mouse-anti-polyHis antibody was also used as a positive control. The results show that although PA20 antibody is able to cross-link 4Ig-B7H3 in a dose-dependent manner (hatched bar), mu-anti-TES7 antibody is unable to cross-link 4Ig-B7H3 at any of the three doses. This was not due to biotin interference of the TES7 epitope, as immobilized biotinylated 4Ig-B7H3 (0 coat condition) was detected by mu-anti-TES7 (solid grey bar).

To further investigate mu-anti-TES binding to 4Ig-B7H3, ELISA crosslinking experiments with a His-tagged 2Ig-B7H3 (R&D Systems) were performed. 5 µg/ml of a capture antibody, mouse anti-poly His antibody, was coated on a 96-well plate as a control, a no coat well (naked well) was also used. The wells with the capture antibody were then blocked with HBSS+1% BSA. 5 µg/ml of 2Ig-B7H3(His) or 4Ig-B7H3(His) was introduced into naked wells or capture antibody-coated wells. As a control, 5 µg/ml of 2Ig-B7H3(Fc) was introduced into naked wells. The plate was then blocked again with HBSS+1% BSA. Then 2 g/ml of biotinylated mu-anti-TES7, BLA8, PA20 or STO5 (another anti-B7H3 antibody that only recognizes the 4Ig form of B7H3) was introduced into the plate. The bound biotinylated antibodies were then detected with streptavidin-HRP using standard protocols.

Figure 6:
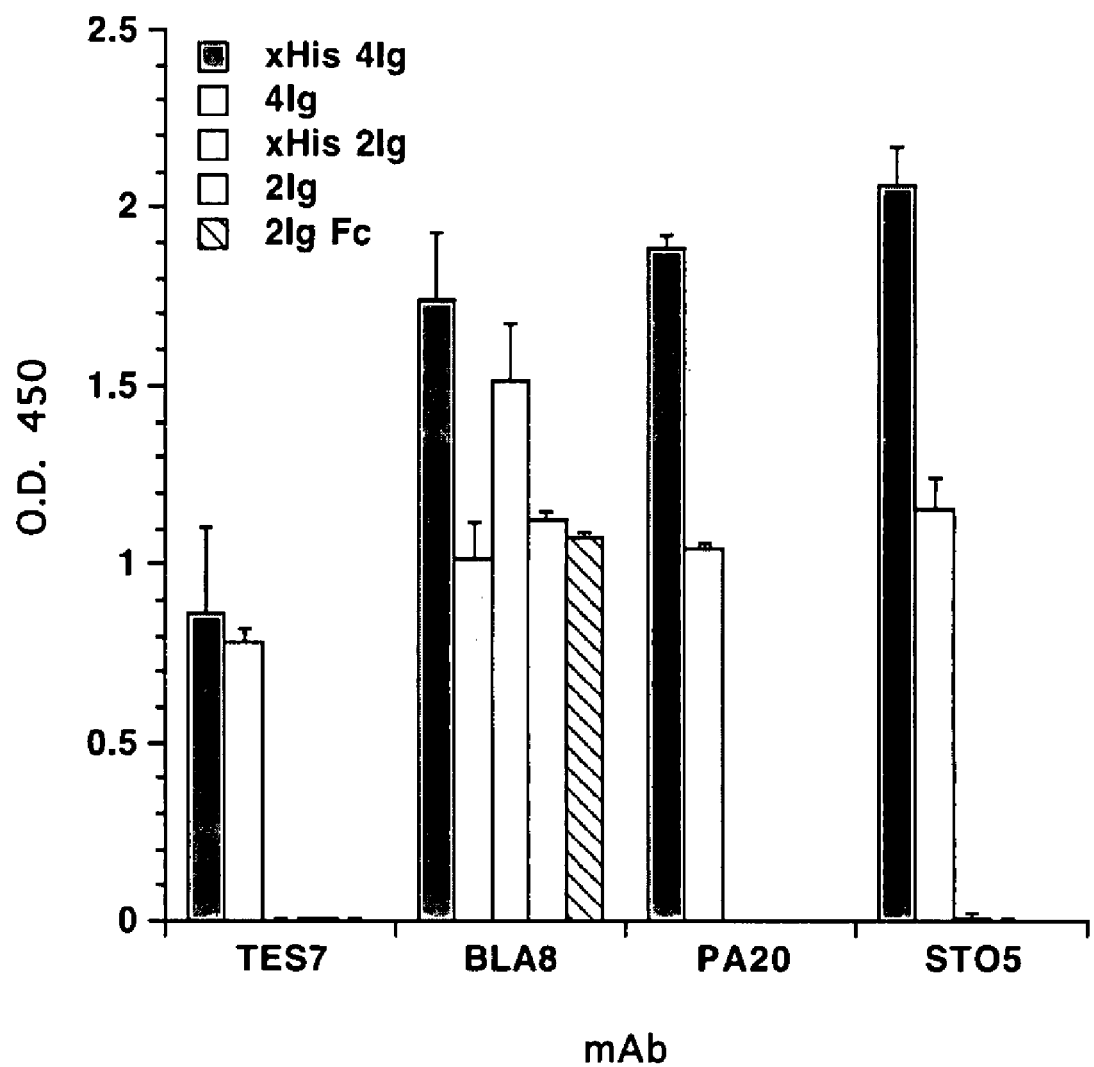
FIG. 6 shows that mu-anti-TES7 reduced MIP-1α (CCL3) secretion in BMC or CSC-BMC co-culture.

As shown in FIG. 6, the BLA8 antibody was able to recognize all five conditions: 2Ig-B7H3(Fc), 2Ig-B7H3 (white bar, 2Ig), crossed-linked 2Ig-B7H3 (pale grey bar, xHis 2Ig), 4Ig-B7H3 (medium grey bar, 4Ig) and crosslinked 4Ig-B7H3 (dark grey bar, xHis 4Ig). With both the 2Ig and the 4Ig forms of B7H3, there was more BLA8 binding when the antigen was cross-linked using the mouse anti-poly His antibody (pale grey bar and dark grey bar) as compared to the non-crossed linked antigen (white bar and medium grey bar).

Both PA20 and STO5 antibodies only bound to 4Ig-B7H3 (medium grey and dark grey bars). Both PA20 and STO5 antibodies also showed increased binding to the crosslinked 4Ig-B7H3 antigen. Interestingly, mu-anti-TES7 bound to 4Ig-B7H3 (medium grey and dark grey bars), but did not show the increased binding to crosslinked 4Ig-B7H3, as seen with PA20 and STO5 antibodies. This result suggests that there is a density component to mu-anti-TES7 binding to 4Ig-B7H3, and that this density component is not seen with certain other 4Ig-B7H3-specific antibodies, such as PA20 and STO5. The results of this experiments also suggest that all three of these 4Ig-B7H3 antibodies tested were specific to epitopes on the unique Ig domains of the 4Ig form of B7H3, since none of the three antibodies recognized crosslinked 2Ig-B7H3 in the ELISA.

To further investigate the antigen-density dependency of mu-anti-TES7 binding to 4Ig-B7H3, a ELISA using a matrix of capture and coating conditions was performed. Two plates were coated with 0.5, 1 or 5 µg/ml of mouse anti-poly His antibody. One of the plates was blocked with HBSS+1% BSA, while the other plate was merely washed. The plates were then incubated with a titration of 4Ig-B7H3(His-tagged), serially diluted from 10 µg/ml to 0.312 µg/ml. The plates were then blocked with HBSS+1% BSA and then detected with 2 µg/ml of biotinylated mu-anti-TES7.

Figure 7:
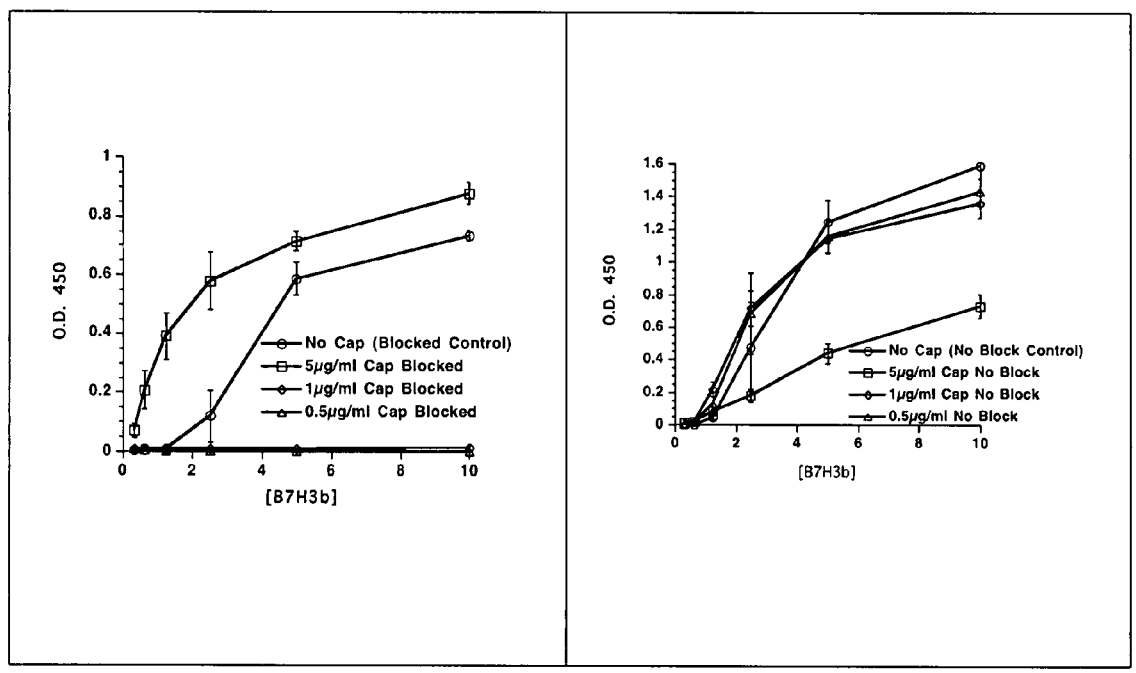
FIG. 7 shows mu-anti-TES7 bound in a concentration dependent manner in the 5 microgram/ml concentration of capture antibody in the capture antibody blocked plate (squares, left hand figure).

As shown in FIG. 7, mu-anti-TES7 bound in a concentration dependent manner in the 5-microgram/ml concentration of capture antibody in the capture antibody blocked plate (squares, left hand figure). Mu-anti-TES7 binding was reduced in the 5-microgram/ml concentration of capture antibody in the no-block capture antibody plate (squares, right hand figure). This result suggests that the no-block capture plate presents a mixture of crosslinked molecules of 4Ig-B7H3 and stand-alone molecules of 4Ig-B7H3 and this mixture of antigen is not optimal for mu-anti-TES7 binding. In the blocked capture plate, only crosslinked 4Ig-B7H3 antigen is present and this density of antigen seems to support mu-anti-TES7 binding.

Also, there was no mu-anti-TES7 binding at the 1 µg/ml and 0.5 µg/ml concentrations of capture antibody condition in the capture antibody blocked plate (FIG. 7, diamond and triangle, left hand figure), whereas there was concentration dependent binding of mu-anti-TES7 in no-block capture antibody plate of the same concentrations of the capture antibody. This result is most likely due to the preference of mu-anti-TES7 for non-crosslinked 4Ig-B7H3 and a lower than optimal density of the antigen (assuming 1 µg/ml of capture antibody can capture 1 µg/ml 4Ig-B7H3). These results are consistent with the other results that show that mu-anti-TES7 binding to 4Ig-B7H3 is density and spatially dependent. This unique density and spatially dependent feature of mu-anti-TES7 binding is likely to influence mu-anti-TES7 binding to 4Ig-B7H3 clustering or density on the cell surface.

Example 11

Internalization of mu-anti-TES7 and Toxin-Conjugated Anti-Mouse IgG

Mab-ZAP (Advanced Targeting Systems, San Diego, Calif.) is an anti-mouse IgG conjugated to saporin, a toxin that inhibits protein synthesis. This toxin is impermeable to the cell membrane. If a monoclonal antibody is bound to a cell-surface antigen that is internalizable, the toxin-conjugate can bind to the bound monoclonal and, thereby, be internalized and eventually kill the cell. Being dependent upon internalization for demonstration of toxic activity, the Mab-ZAP can serve to evaluate whether or not a given surface antigen will serve as a suitable target for any toxin that is dependent upon internalization to express cell toxic effects. As such, the Mab-ZAP serves as a model for such internalization-dependent toxins such as maytansinoids and chalicheamicins.

For testing the internalization of mu-anti-TES7 and saporin conjugated anti-mouse IgG by tumor cells and effect of killing the tumor cells after internalization of saporin, human pancreatic carcinoma cells, HS 700T cell line, were removed from stock flasks with 10 mM EDTA and centrifuged. Cells were resuspended at 50,000/ml in appropriate medium and 100 µl plated per well in 96 well plates. Antibody mu-anti-TES7 was added immediately to appropriate wells as a 10× concentrate, to make a final concentration of 10 ug/ml. After 15 minutes at room temperature Mab-ZAP (Cat. # IT-04, Advanced Targeting Systems, San Diego Calif.) was added to appropriate wells as 10× concentrate, to make final concentrations from 0.001 nM to 10 nM. After 4 days growth, MTT was added (stock 5 mg/ml PBS, 1:10 dilution in well) for 4 hrs at 37° C. The medium was then removed from all wells and 100 µl/well DMSO was added. The plates were gently swirled to solubilize the blue MTT precipitate and the plates were read at O.D. 540 nm.

There was a decrease in MTT staining in HS 700T cells in the presence of mu-anti-TES7 as compared to staining in the absence of mu-anti-TES7. This indicates that the growth of HS 700T cells was inhibited in the presence of mu-anti-TES7 and Mab-ZAP and these results are indicative of mu-anti-TES7 and toxin-conjugated anti-mouse IgG were internalized in HS 700T cells.

Results of an internalization experiment according to the methods of this Example are shown in FIG. 1.

Example 12

Effect of mu-anti-TES7 on the Human Colorectal Adenocarcinoma HT29 Cell Line

The ability of the antibodies to reduce cell number in vitro when grown as a monolayer can be assessed using cell monolayers grown in the presence or absence of varying amounts of test or control purified antibody and the change in cell number assessed using MTT. MTT is a dye that measures the activity of mitochondrial enzymes and correlates with relative viable cell number. Cells of interest were plated and grown in F12/DMEM (1:1) growth medium supplemented with 10% fetal bovine serum in 96 well plates. HT29 cell line was plated at 1500 cells/well in triplicate wells of a 96 well dish. Immediately after plating, mu-anti-TES7 was added. The cells were incubated at 37° C. in a humidified incubator at 5% $CO_2$/air for 6 days. At the end of the assay, MTT was dissolved in PBS (5 mg/ml) and added directly to wells at 1:10 dilution. Plates were placed back in incubator for 4 hours. After the incubation, medium was removed and 100 µl DMSO was added to solubilize the MTT precipitate. Plates were read at 540 on plate reader.

Figure 2:
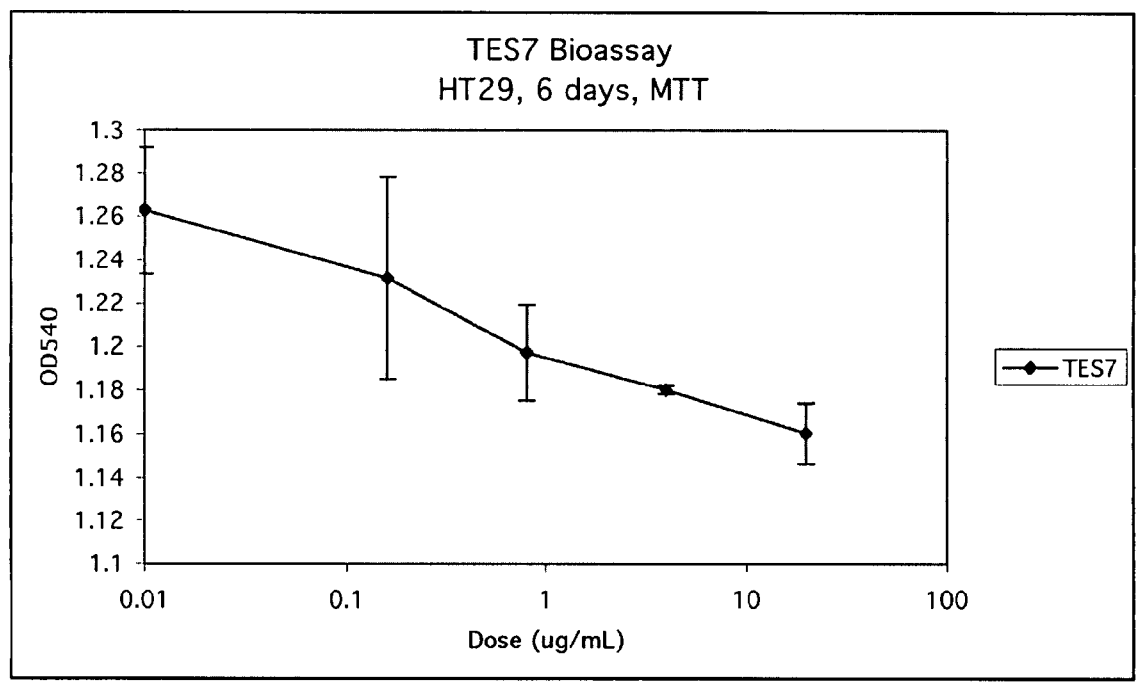
FIG. 2 shows the graphed results of an experiment illustrating in vitro inhibition of the human colorectal adenocarcinoma cell line, HT29, grown as a monolayer by an anti-TES7 antibody, mu-anti-TES7.

FIG. 2 shows a representative graphed result of mu-anti-TES7, at varying concentrations, on HT29 cell line. Other bioassays with HT29 confirmed the growth inhibitory effects of mu-anti-TES7. In data not shown, mu-anti-TES7 was also shown to inhibit growth of the NCI-H322M lung carcinoma line and the MDA361 breast adenocarcinoma.

Example 13

In Vivo Effects of mu-anti-TES7 in Both Sub-Renal Capsule Xenograft and Subcutaneous Xenograft Models The ability of mu-anti-TES7 to reduce tumor growth in vivo was tested in both the sub-renal capsule xenograft and subcutaneous xenograft models. Both xenograft models are well known in the art and standard protocols are suitable for testing in vivo tumor growth inhibition of mu-anti-TES7 antibodies.

For the sub-renal capsule xenograft model, female nu/nu homozygous mice (Charles River Laboratories, Wilmington, Mass.) were used. Animals were 6 to 8 weeks of age at the start of the study, with an average weight of 20-30 grams. A prostate carcinoma cell line was used in this study. Cells were embedded into collagen buttons for implantation at the sub-renal capsule site. After implantation, the mice were allowed to recover from the surgery. For the treatment group, mu-anti-TES7 was diluted in PBS to 50 mg/kg concentration. Control groups received PBS. Dosing was initiated on Day 2 following implantation and doses 50 mg/kg mu-anti-TES7 and PBS control were administered three times weekly as single rapid injections into the intraperitoneal cavity. At the end of the study, the mice were sacrificed and the tumors and adjacent tissue were removed for human DNA quantification.

qRT-PCR is well known in the art and standard protocols were used. Briefly, the excised tumors from treated and control mice were incubated in a digestion buffer containing proteinase K (1.45 mg/ml) and RNase A (0.07 mg/ml) overnight at 55° C. for DNA isolation. Genomic DNA was isolated from tumors using the Wizard SV Genomic DNA Purification System (Promega, Wisconsin) according to manufacturer's instructions. Each DNA sample was resuspended in a final volume of 200 μl. Using primers specific for the human ribosomal gene RPL19, human DNA from the tumor samples were quantified using real-time PCR on an Applied Biosystems SDS7000 system (Foster City, Calif.). Sample DNA concentrations were interpolated from the standard curve. Each tumor sample was analyzed in triplicate PCR reactions and average DNA concentrations were determined. Average DNA concentration and standard error of the mean was determined for each group of tumor samples. Tumor growth inhibition was calculated as the absolute value of: [(average ng of human DNA of treated group/average ng of human DNA of PBS control group)×100]−100.

Mu-anti-TES7 treated tumors showed 65.7% tumor growth inhibition as compared to PBS treated tumors using a prostate carcinoma cell line. Similar tumor growth inhibition was seen in mu-anti-TES7 treated tumors using a rectal carcinoma cell line, lung carcinoma cell line, H322M and colorectal carcinoma cell line, HT-29.

The in vivo tumor growth inhibitory effects of mu-anti-TES7 were also examined using a subcutaneous xenograft model. The subcutaneous xenograft model is well known in the art and other standard protocols would also be suitable. Tumor cells mixed with 50% Matrigel® were injected subcutaneously at a volume of 0.1 ml in the flank or the back of the nice of mice. Twice a week dosing of either control PBS or 50 mg/kg mu-anti-TES7 was initiated 10 days post tumor inoculation (when the tumor volume was approximately 75-100 mm). Tumors were measured by digital caliper in three dimensions (height×length×width) and the tumor volume was calculated as one-half the product of the three measurements. Average tumor volumes and standard error of the mean were determined for each group at each measurement. Statistical significance was determined using two-way ANOVA with Bonferroni posttests (Graphpad Prism version 4.0c for Macintosh, Graphpad Software, San Diego Calif., USA). Tumor growth inhibition was calculated as the absolute value of: [(average tumor volume of treated group/average tumor volume of PBS control group)×100]−100.

Figure 8:
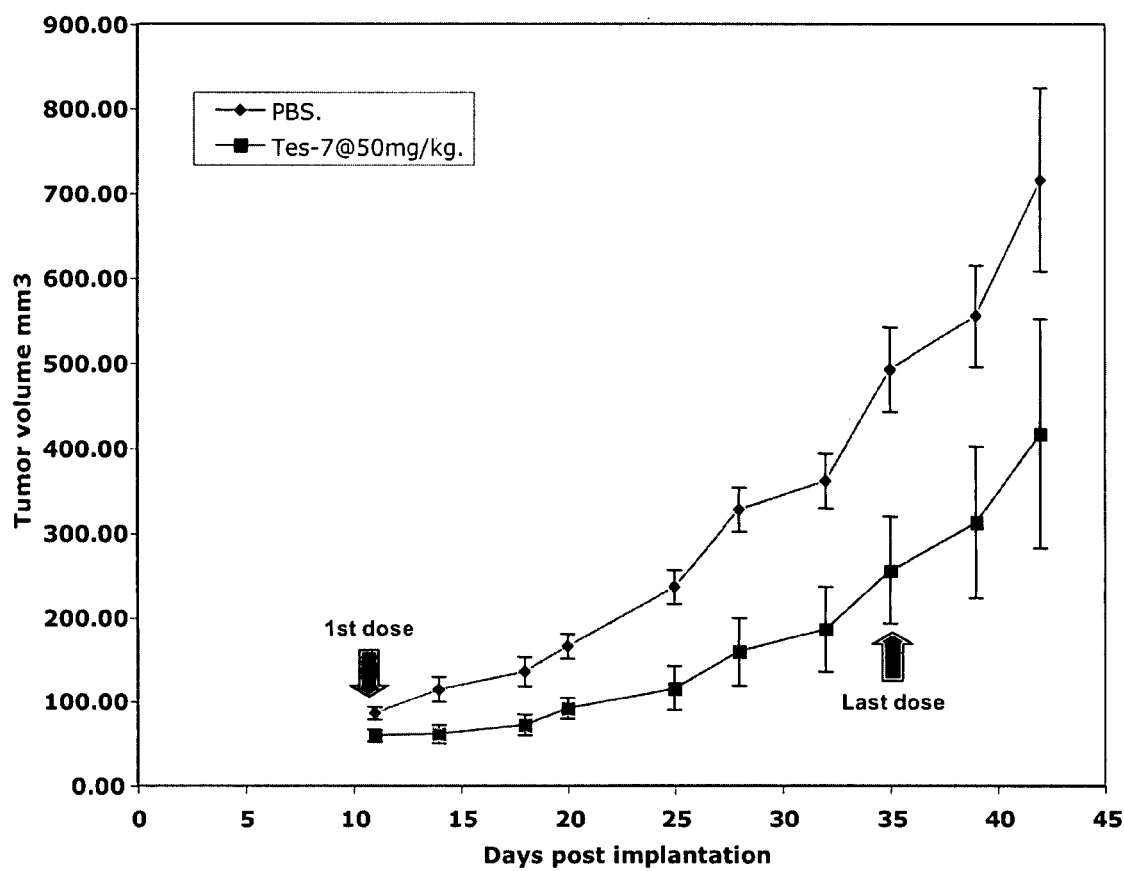
FIG. 8 shows the ability of mu-anti-TES7 to reduce tumor growth in vivo was tested in subcutaneous xenograft models.

Pancreatic adenocarcinoma cell line, Hs700T was used in the subcutaneous xenograft study. 5 million cells were injected according to the protocol described above and mu-anti-TES7 antibody dosing began 11 days after tumor implantation. The last dose was given on Day 35 post tumor implantation and tumor measurements continued for one more week post-dosing. The results of this study are shown in FIG. 8 and statistical analysis is summarized below in Table 9.

Mu-anti-TES7 treated tumors were between 40-50% smaller when compared to PBS control on all days measured after Day 18 post-tumor implantation. Significant (p value less than 0.05) tumor growth inhibition was seen on mu-anti-TES7 treated tumors at Day 35, 39 and 42 post-tumor implantation. This result is consistent with tumor growth inhibition observed using the sub-renal capsule xenograft model and also with growth inhibition of tumor cells in vitro.

TABLE 9

Statistical Analysis of mu-anti-TES7 Efficacy on Established Hs700T Subcutaneous Xenograft.

| Days Post Tumor Inoculation | Day 11 | | Day 14 | | Day 18 | | Day 20 | | Day 25 | |
|---|---|---|---|---|---|---|---|---|---|---|
| | % TGI | p = | % TGI | p = | % TGI | p = | % TGI | p = | % TGI | p = |
| 50 mg/kg (established) | - | - | - | - | 46.8 | ns | 44.6 | ns | 51.3 | ns |

| Days Post Tumor Inoculation | Day 28 | | Day 32 | | Day 35 | | Day 39 | | Day 42 | |
|---|---|---|---|---|---|---|---|---|---|---|
| | % TGI | p = | % TGI | p = | % TGI | p = | % TGI | p = | % TGI | p = |
| 50 mg/kg (established) | 51.7 | Ns | 48.7 | ns | 47.9 | <0.05 | 43.6 | <0.05 | 41.7 | <0.001 |

*Shaded boxes represent % tumor growth inhibition (TGI) with p < 0.05.

Example 14

Effect of mu-anti-TES7 on Cytokines

Cytokine signaling was examined in assays using the following cancer stem cell (CSC) lines: BRCA0312 (Clone #2, breast CSC), CA130 (lung CSC), CRCA1115 (colon CSC), PA9926 (pancreatic CSC), PRCA0312-58 & PRCA629A (prostate CSC), RECA1208 (colorectal CSC). Non-irradiated bone marrow stroma cells (BMC) were obtained from Lonza (Cat # 2M-302).

Bone marrow stroma cells (BMC) were obtained at $6\times10^4$. Cells were cultured with 10 percent FBS for 2 days. Cells were washed twice, serum starved for 4 hours, then washed twice more. A layer of cancer stem cells (CSC) was added, at 1-2×10e4, with or without 50 microgram/ml murine IgG antibody control or anti-TES7 in Basal F12 DMEM for 3 days. Cell supernatant was saved for Luminex multiplex assays.

Luminex multiplex assays were performed (Upstate), using 35 soluble factors: Growth factors: EGF, FGF-2, G-CSF, GM-CSF, TNF alpha, PDGF-AA, PDGF-AB/BB & VEGF. Cytokines: IFN gamma, IL-1 alpha, IL-1 beta, IL-2, IL-3, IL-4, IL-5, IL-6, IL-7, IL-10, IL-12(p40), IL-12(p70), IL-13, IL-15 & IP-10. Chemokines: Eotaxin (CCL11), IL-8 (CXCL8), MCP-1 (CCL2), MIP-1 alpha (CCL3) & RANTES (CCL5). Other soluble factors used include: FasL, Flt-3L, IL-IR alpha, IL-6R alpha, ICAM-1, gp130 & VCAM-1.

When sample Media Fluorescent Unit (MFU) was $\geq 100$ (2-5-fold above background), a comparison was made between TES7 and Mouse IgG control. When the comparison yielded $\geq 2$-fold change, up/downregulation was assigned accordingly. The result was further evaluated by ANOVA with Tukey post test, and statistical significance was considered when $p<0.05$.

Figure 9:
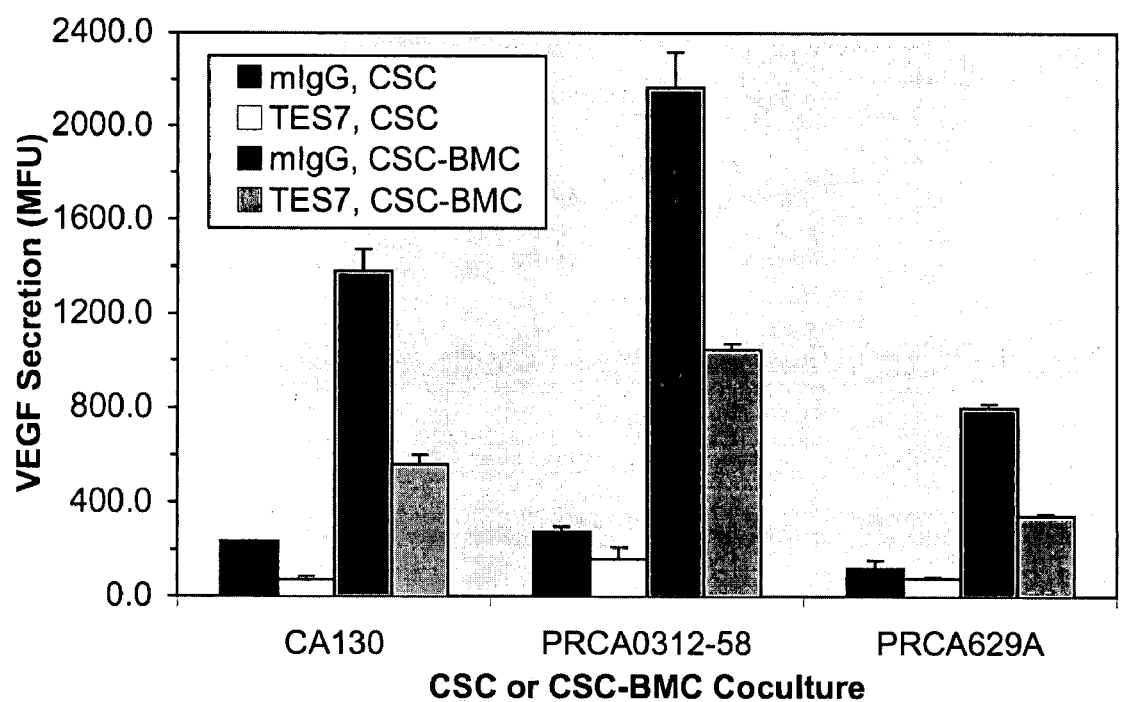
FIG. 9 shows reduction by mu-anti-TES7 of VEGF secretion in CSC-BMC co-culture (VEGF incidence: 3/7).
Figure 10:
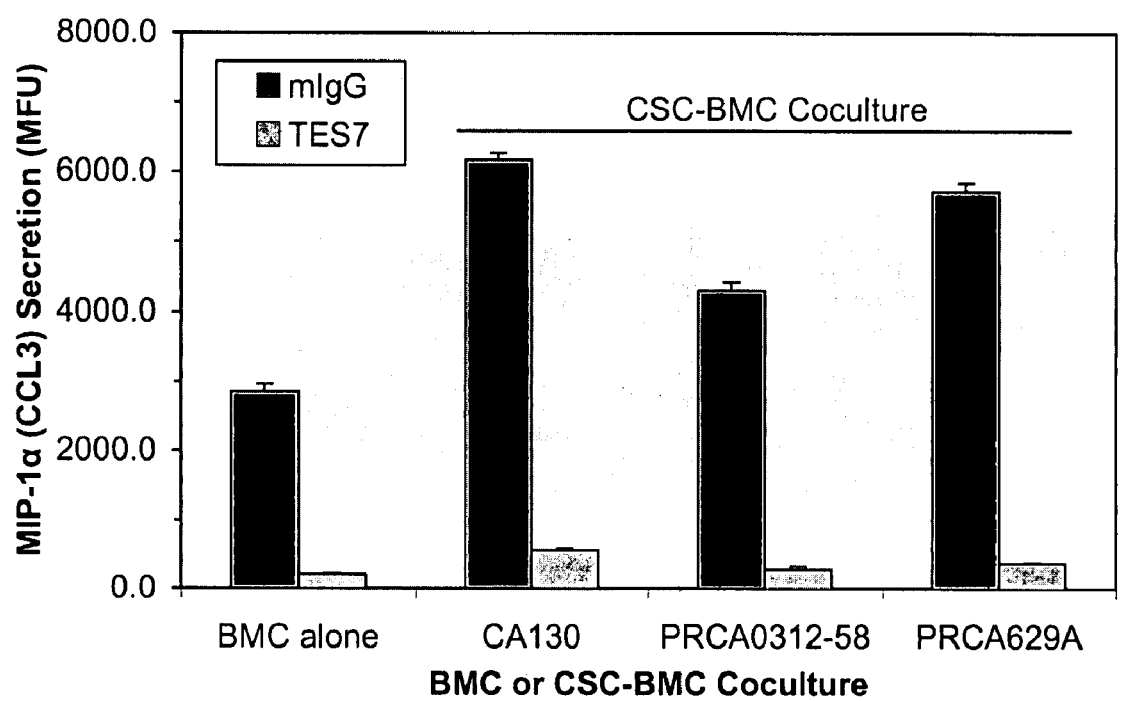
FIG. 10 shows reduction by mu-anti-TES7 of MIP-1 alpha (CCL3) secretion in BMC or CSC-BMC co-culture (CCL3, incidence: 6/7).

As shown in FIG. 9, TES7 reduced VEGF secretion in CSC-BMC co-culture (VEGF incidence: 3/7). As shown in FIG. 10, TES7 reduced MIP-1 alpha (CCL3) secretion in BMC or CSC-BMC co-culture (CCL3, incidence: 6/7). VEGF is a cytokine known to involved in tumor vascularization. MIP-1 alpha (CCL3) is a cytokine known to play a role in tumor biology (see e.g. Bieche et al, Clin Cancer Res, 2004, Yang et al, Int J Cancer, 2006, and Ryschich et al, Cancer Res, 2006).

The cytokine profile analysis provides evidence that the murine anti-TES7 antibody is able to modulate cytokine pathways and cytokine signaling across several cell lines. This provides new insight into signaling mechanisms that are capable of driving tumor growth, and the ability to identify growth modulatory antibodies according to the methods taught herein that would otherwise be missed in standard growth assays.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

---

We claim:

1. A substantially purified immunoglobulin polypeptide or an antigen-binding fragment thereof, that specifically binds to 4Ig form of B7H3 expressed on a cancer cell, but does not specifically bind to 2Ig B7H3 and is unable to cross-link 4Ig-B7H3.

2. The purified immunoglobulin polypeptide or antigen binding fragment of claim 1, wherein said cancer cell is selected from the group consisting of a cancer cell from: an adrenal gland tumor, an AIDS-associated cancer, an alveolar soft part sarcoma, an astrocytic tumor, a bladder cancer, a bone cancer, a brain or spinal cord cancer, a metastatic brain tumor, a breast cancer, a carotid body tumor, a cervical cancer, a chondrosarcoma, a dhordoma, a chromophobe renal cell carcinoma, a clear cell carcinoma, a colon cancer, a colorectal cancer, a cutaneous benign fibrous histiocytoma histiocytomas, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a head and neck cancer, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome cell, a neuroblastoma, a neuroendocrine tumor, an ovarian cancer, a pancreatic cancer, a papillary thyroid carcinoma, a parathyroid tumor, a pediatric cancer cell, a peripheral nerve sheath tumor, a phaeochromocytoma, a pituitary tumor, a prostate cancer, a posterious unveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

3. A pharmaceutical composition comprising the purified immunoglobulin or antigen-binding fragment of claim 1, together with a pharmaceutically acceptable carrier.

4. The pharmaceutical composition of claim 3, wherein the composition comprises an additional therapeutic moiety.

5. A method for delivering a chemotherapeutic agent to a cancer cell comprising administering a composition comprising the polypeptide or antigen-binding fragment thereof of claim 1 associated with the chemotherapeutic agent, wherein said cancer cell is selected from the group consisting of a cancer cell from: an adrenal gland tumor, an AIDS-associated cancer, an alveolar soft part sarcoma, an astrocytic tumor, a bladder cancer, a bone cancer, a brain or spinal cord cancer, a metastatic brain tumor, a breast cancer, a carotid body tumor, a cervical cancer, a chondrosarcoma, a dhordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a head and neck cancer, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome cell, a neuroblastoma, a neuroendocrine tumor, an ovarian cancer, a pancreatic cancer, a papillary thyroid carcinoma, a parathyroid tumor, a pediatric cancer cell, a peripheral nerve sheath tumor, a phaeochromocytoma, a pituitary tumor, a prostate cancer, a posterious unveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

6. The method of claim 5, wherein the chemotherapeutic agent is administered to an individual.

7. The method of claim 5, wherein the polypeptide is produced by the hybridoma having ATCC deposit number PTA-7093 or progeny thereof.

8. A method for detecting the presence or absence of a cancer cell in an individual comprising contacting cells from the individual with the polypeptide or antigen-binding fragment thereof of claim 1, and detecting a complex of TES7 from the cells and the antibody, if any, wherein said cancer cell is selected from the group consisting of a cancer cell from: an adrenal gland tumor, an AIDS-associated cancer, an alveolar soft part sarcoma, an astrocytic tumor, a bladder cancer, a bone cancer, a brain or spinal cord cancer, a metastatic brain tumor, a breast cancer, a carotid body tumor, a cervical cancer, a chondrosarcoma, a dhordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a head and neck cancer, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome cell, a neuroblastoma, a neuroendocrine tumor, an ovarian cancer, a pancreatic cancer, a papillary thyroid carcinoma, a parathyroid tumor, a pediatric cancer cell, a peripheral nerve sheath tumor, a phaeochromocytoma, a pituitary tumor, a prostate cancer, a posterious unveal melanoma, a rare hematologic disorder, a renal metastatic cancer, a rhabdoid tumor a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

9. An isolated antibody produced by the host cell line having ATCC deposit number PTA-7093 or progeny thereof.

10. An isolated antibody or an antigen-binding fragment thereof that specifically binds to 4Ig form of B7H3, the antibody comprising a heavy chain variable region comprising the three heavy chain CDRs and a light chain variable region comprising the three light chain CDRs from the antibody produced by the host cell line having ATCC deposit number PTA-7093.

11. The isolated antibody or the antigen-binding fragment of claim 10, wherein the isolated antibody is a humanized antibody.

12. The isolated antibody or the antigen-binding fragment of claim 11, wherein the heavy variable region of the humanized antibody comprises the amino acid sequence of SEQ ID NO:7 or 8.

13. The isolated antibody or the antigen-binding fragment of claim 11, wherein the light variable region of the humanized antibody comprises the amino acid sequence of SEQ ID NO:3 or 4.

14. The isolated antibody or the antigen-binding fragment of claim 10, wherein the isolated antibody is a chimeric antibody comprising the heavy and light variable regions from the antibody produced by the host cell line having ATCC deposit number PTA-7093.

15. The isolated antibody or the antigen-binding fragment of claim 14, wherein the chimeric antibody comprises a heavy chain constant region from the heavy chain constant region from a human antibody, and a light chain constant region from the light chain constant region of a human antibody.

16. The isolated antibody or the antigen-binding fragment of claim 10, wherein the antigen-binding fragment is selected from the group consisting of a Fab, a Fab', a F(ab')$_2$ and a Fv.

17. An isolated antibody produced by the host cell line having ATCC deposit number PTA-8576 or progeny thereof.

18. An isolated antibody or an antigen-binding fragment thereof that specifically binds to 4Ig form of B7H3, the antibody comprising a heavy chain variable region comprising the three heavy chain CDRs and a light chain variable region comprising the three light chain CDRs from the antibody produced by the host cell line having ATCC deposit number PTA-8576.

19. The isolated antibody or the antigen-binding fragment of claim 18, wherein the isolated antibody is a humanized antibody.

20. The isolated antibody or the antigen-binding fragment of claim 18, wherein the isolated antibody is a chimeric antibody comprising the heavy and light variable regions from the antibody produced by the host cell line having ATCC deposit number PTA-8576.

21. The isolated antibody or the antigen-binding fragment of claim 20, wherein the chimeric antibody comprises a heavy chain constant region from the heavy chain constant region from a human antibody, and a light chain constant region from the light chain constant region of a human antibody.

22. The isolated antibody or the antigen-binding fragment of claim 18, wherein the antigen-binding fragment is selected from the group consisting of a Fab, a Fab', a F(ab')$_2$ and a Fv.

* * * * *

SEQUENCE LISTING

```
<160> NUMBER OF SEQ ID NOS: 8

<210> SEQ ID NO 1
<211> LENGTH: 107
<212> TYPE: PRT
<213> ORGANISM: Mus musculus

<400> SEQUENCE: 1

Asp Val Gln Ile Thr Gln Ser Pro Ser Tyr Leu Ala Ala Ser Pro Gly
1               5                   10                  15

Glu Thr Ile Thr Val Asn Cys Arg Ala Ser Glu Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Met Tyr Tyr Cys His Gln His Asn Glu Phe Pro Leu
                85                  90                  95

Thr Phe Gly Ala Gly Thr Lys Leu Glu Leu Lys
            100                 105

<210> SEQ ID NO 2
<211> LENGTH: 107
<212> TYPE: PRT
<213> ORGANISM: Homo sapiens
```

```
<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln His Asn Glu Phe Pro Leu
                85                  90                  95

Thr Phe Gly Gly Gly Thr Lys Val Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Asp Ile Gln Ile Thr Gln Ser Pro Ser Ser Leu Ser Ala Ser Val Gly
1               5                   10                  15

Asp Arg Val Thr Ile Thr Cys Arg Ala Ser Glu Ser Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys His Gln His Asn Glu Phe Pro Leu
                85                  90                  95

Thr Phe Gly Gly Gly Thr Lys Val Glu Ile Lys
            100                 105

<210> SEQ ID NO 5
<211> LENGTH: 116
<212> TYPE: PRT
<213> ORGANISM: Mus musculus

<400> SEQUENCE: 5

Gln Val Gln Leu Gln Gln Ser Gly Pro Glu Leu Val Lys Pro Gly Thr
 1               5                  10                  15

Ser Val Arg Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
            35                  40                  45

Gly Trp Ile Tyr Pro Gly Asn Val Asn Thr Lys Tyr Asn Glu Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Tyr Phe Phe Asp Gln Trp Gly Gln Gly Thr Thr Leu
            100                 105                 110

Thr Val Ser Ser
        115

<210> SEQ ID NO 6
<211> LENGTH: 121
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ile Leu Thr Gly Leu Asn Trp Phe Asp Pro Trp Gly
            100                 105                 110

Gln Gly Thr Leu Val Thr Val Ser Ser
        115                 120

<210> SEQ ID NO 7
<211> LENGTH: 116
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Tyr Pro Gly Asn Val Asn Thr Lys Tyr Asn Glu Asn Phe
        50                  55                  60

Lys Gly Arg Ala Thr Ile Thr Ala Asp Lys Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

Ala Arg Gly Gly Tyr Phe Phe Asp Gln Trp Gly Gln Gly Thr Leu Val
            100                 105                 110

Thr Val Ser Ser
            115

<210> SEQ ID NO 8
<211> LENGTH: 116
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Asn Val Asn Thr Lys Tyr Asn Glu Asn Phe
        50                  55                  60

Lys Gly Lys Ala Thr Leu Thr Ala Asp Lys Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

Ala Arg Gly Gly Tyr Phe Phe Asp Gln Trp Gly Gln Gly Thr Leu Val
            100                 105                 110

Thr Val Ser Ser
            115
```